(12) United States Patent
Rokhsar et al.

(10) Patent No.: US 11,091,758 B2
(45) Date of Patent: Aug. 17, 2021

(54) METHODS FOR LABELING DNAA FRAGMENTS TO RECONSTRUCT PHYSICAL LINKAGE AND PHASE

(71) Applicant: The Regents of the University of California, Oakland, CA (US)

(72) Inventors: Daniel Rokhsar, Berkeley, CA (US); Richard E. Green, Jr., Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 1291 days.

(21) Appl. No.: 15/103,821

(22) PCT Filed: Dec. 11, 2014

(86) PCT No.: PCT/US2014/069642
§ 371 (c)(1),
(2) Date: Jun. 10, 2016

(87) PCT Pub. No.: WO2015/089243
PCT Pub. Date: Jun. 18, 2015

(65) Prior Publication Data
US 2016/0312213 A1    Oct. 27, 2016

Related U.S. Application Data

(60) Provisional application No. 61/914,855, filed on Dec. 11, 2013.

(51) Int. Cl.
*C12N 15/10* (2006.01)
*C12Q 1/6844* (2018.01)
(Continued)

(52) U.S. Cl.
CPC ....... *C12N 15/1065* (2013.01); *C12Q 1/6844* (2013.01); *C12Q 1/6855* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS 8,076,070 B2   12/2011   Chen et al.
8,741,577 B2   6/2014    Graneli et al.
(Continued)

FOREIGN PATENT DOCUMENTS

WO   2005/001113 A2   1/2005
WO   2010/036323 A1   4/2010
(Continued)

OTHER PUBLICATIONS

Dostie et al (Genome Research 16:1299-309) (Year: 2006).*
(Continued)

*Primary Examiner* — Christopher M Gross
(74) *Attorney, Agent, or Firm* — Gavrilovich, Dodd & Lindsey LLP

(57) ABSTRACT

The disclosure provides for methods to form compact cross-linked polynucleotide/protein structures that can then be labeled using a barcoded oligonucleotide array in order to reconstruct physical linkage and/or genomic proximity (and phase) of polynucleotide fragments.

17 Claims, 9 Drawing Sheets

(51) Int. Cl.
*C12Q 1/6855* (2018.01)
*C12Q 1/6883* (2018.01)

(56) References Cited

U.S. PATENT DOCUMENTS

| | | | |
|---|---|---|---|
| 10,089,437 B2* | 10/2018 | Green, Jr. | C12Q 1/6869 |
| 2003/0228627 A1 | 12/2003 | Emerson et al. | |
| 2005/0260625 A1 | 11/2005 | Wang | |
| 2006/0040297 A1* | 2/2006 | Leamon | B01L 3/5027 |
| | | | 435/6.18 |
| 2007/0231817 A1 | 10/2007 | De Laat et al. | |
| 2008/0233101 A1* | 9/2008 | Sauer | C12N 15/63 |
| | | | 424/94.61 |
| 2009/0269771 A1 | 10/2009 | Schroeder | |
| 2011/0256593 A1 | 10/2011 | Hsieh et al. | |
| 2011/0300537 A1 | 12/2011 | Slepnev | |
| 2011/0306504 A1 | 12/2011 | Xiao et al. | |
| 2012/0330559 A1 | 12/2012 | Jiang et al. | |
| 2013/0005585 A1 | 1/2013 | Anderson et al. | |
| 2013/0045872 A1 | 2/2013 | Zhou et al. | |
| 2013/0310548 A1 | 11/2013 | Park | |
| 2014/0141982 A1 | 5/2014 | Jacobson et al. | |
| 2014/0220587 A1 | 8/2014 | Green et al. | |
| 2015/0363550 A1 | 12/2015 | Green et al. | |

FOREIGN PATENT DOCUMENTS

| | | |
|---|---|---|
| WO | 2012/106546 A2 | 8/2012 |
| WO | 2014/121091 A1 | 8/2014 |

OTHER PUBLICATIONS

Vakoc et al (Molecular Cell 17:453-62) (Year: 2005).*
Monson-Miller et al (BMC Genomics 13:72 13 pages) (Year: 2012).*
Belton et al, "Hi-C: A comprehensive technique to capture the conformation of genomes", Methods, vol. 58, No. 3, Nov. 1, 2012, pp. 268-276.
Diez Schlereth, D., Extended European Search Report, European Patent Office, Application No. 19155684.4, dated Jul. 19, 2019.
Ferraiuolo et al., "From cells to 1-15 chromatin: Capture snapshots of genome organization with 5C technology", Methods, vol. 58, No. 3, Nov. 1, 2012, pp. 255-267.
Sexton et al., "Sensitive detection of chromatin coassociations using enhanced chromosome conformation capture on chip", Nature Protocols, vol. 7, No. 7, Jun. 21, 2012, pp. 1335-1350.
Splinter et al., "Determining long-range chromatin interactions for selected genomic sites using 4C-seq technology: From fixation to computation", Methods, vol. 58, No. 3, Nov. 1, 2012, pp. 221-230.
Stadhouders et al., "Multiplexed chromosome conformation capture sequencing for rapid genome-scale high-resolution detection of long-range chromatin interactions", Nature Protocols, vol. 8, No. 3, Feb. 14, 2013, pp. 509-524.
Belton et al., "Hi-C; A comprehensive techique to capture the conformation of genomes", Methods, vol. 58, No. 3, Nov. 1, 2012, pp. 268-276.
Diez Schlereth, D., Extended European Search Report, Application No. 14870464.6, European Patent Office, dated Apr. 6, 2017.
Diez Schlereth, D., Office Action, Application No. 14870464A, European Patent Office, dated Nov. 27, 2017.
Ferraiuolo et al., "Mapping chromatin interactions with 5c technology", Methods, Nov. 2012, vol. 58(3), pp. 1-34.
Sexton, Tom et al., "Sensitive detection of chromatin coassociations using enhanced chromosome conformation rapture on chip", Nature Protocols, vol. 7, No. 7 Jun. 21, 2012, pp. 1335-1350.
Splinter et al., "Determining long-range chromatin interactions for selected genomic sites using 4C-seq technology: From fixation to computation", Methods, vol. 58, Nov. 2012, pp. 221-230.
Stadhouders, Ralph et al., "Multiplexed chromosome conformation capture sequencing for rapid genome-scale high-resolution detection of long-range chromatin interactions," Nature Protocols, vol. 8, No. 3, Feb. 14, 2013, pp. 509-524.
Copenfieaver, Blaine R., International Search Report and Written Opinion, PCT/US2014/069642, U.S. Patent and Trademark Office, dated Mar. 31, 2015.
Nickitas-Etienne, Atthina, International Preliminary Report on Patentability and Written Opinion, PCT/US2014/069642,The International Bureau of WIPO, dated Jun. 23, 2016.
Peters et al., "Accurate whole-genome sequencing and haplotyping from 10 to 20 human cells," Nature, 487:190-195, Jul. 12, 2012.

* cited by examiner

METHODS FOR LABELING DNAA FRAGMENTS TO RECONSTRUCT PHYSICAL LINKAGE AND PHASE

CROSS REFERENCE TO RELATED APPLICATIONS

This application is a U.S. National Stage Application filed under 35 U.S.C § 371 and claims priority to International Application No. PCT/US2014/069642, filed Dec. 11, 2014, which application claims priority under 35 U.S.C. § 119 from Provisional Application Ser. No. 61/914,855, filed Dec. 11, 2013, the disclosures of which are incorporated herein by reference in their entirety.

TECHNICAL FIELD

The disclosure provides for methods to label polynucleotide fragments with a barcode sequence from an array in order to reconstruct physical linkage and phase and/or to determine genomic proximity.

BACKGROUND

In genome analysis it is useful to identity DNA segments that are close to each other on the same chromosome for the purposes of linking sequences together, identifying structural variations, and properly phasing genetic variants.

SUMMARY

The methods disclosed herein take advantage of the ability to form polypeptide-nucleic acid complexes, for example by (reversibly) cross-linking chromatin or other polypeptide-nucleic acid complexes or otherwise binding a polypeptide or polypeptides to a nucleic acid molecule in a way that physically connects different parts of a long polynucleotide, such as through chemical linkage. When the polypeptide-nucleic acid complexes are formed, such as via crosslinking of chromatin or reconstituted chromatin or via otherwise binding a polypeptide to a nucleic acid molecule, the complexes behave as polymer units and can be manipulated without fear that shearing or cleaving the nucleic acid molecule will result in loss of physical linkage or phase information of its sequence constituents, since the nucleic acid is in a compact, stable and redundantly bound (such as multiply cross-linked) form. The disclosure provides for methods using these redundantly bound polypeptide-nucleic acid complexes, such as cross-linked polypeptide-polynucleotide complexes, with a barcode tagging mechanism such as a barcoded oligonucleotide array in order to generate and identify polynucleotide fragments of a size suitable for sequencing that are tagged at their termini to indicate whether they are related by physical linkage and proximity (including phase).

The disclosure provides a method to label polynucleotide fragments with a barcode, comprising cross-linking one or more polynucleotides with chromatin or reconstituted chromatin in order to form one or more polynucleotide-polypeptide globs; generating a plurality of sticky ends from digesting the one or more globs with one or more restriction enzymes; contacting the one or more restriction digested globs with one or more sectors of a barcoded oligonucleotide array, wherein the oligonucleotides of the array comprise a nucleotide sequence for a sequencing primer, unique barcode sequence for each sector, and a short sticky end adapter sequence; annealing the sticky ends of one or more restriction digested globs with complementary sticky end adapter sequences of the oligonucleotide array; polymerizing the annealed sticky ends with a strand-displacing polymerase so as to form an extended polynucleotide which comprises sequences for the sequencing primer, unique sector barcode, annealed sticky ends and the polynucleotide from the one or more globs; and cleaving the extended polynucleotides from the array to generate barcoded polynucleotide fragments. In one embodiment, the one or more polynucleotides are double stranded DNA. In another embodiment, the double stranded DNA is about 1 megabase in length. In any of the foregoing embodiments, the polynucleotide-polypeptide globs are formed in vitro using reconstituted chromatin. In still other embodiments of the foregoing crosslinks of the polynucleotide-polypeptide globs are chemically fixed using formaldehyde and/or psoralen. In further embodiments of any of the foregoing one or more polynucleotide-polypeptide globs is digested with a restriction enzyme that forms a sticky end. In a yet a further embodiment, one or more polynucleotide-polypeptide globs is digested with a restriction enzyme that recognizes a 4, 5 or 6 base pair restriction site and forms a sticky end. In any of the foregoing embodiments, the barcoded oligonucleotide array comprises anywhere from 1 to greater than a million sectors, wherein the oligonucleotides from each sector comprise a unique barcode sequence. In still further embodiments of any of the foregoing embodiments, the sticky ends and sticky end adapter sequences are annealed under stringent conditions. In yet another embodiment of any of the foregoing the strand-displacing polymerase is selected from phi29, Bst DNA Polymerase (large fragment), Bsu DNA Polymerase (large fragment), Deep Vent$_R$™ DNA Polymerase, Deep Vent$_R$™ (exo-)DNA Polymerase, and DNA Polymerase I (Klenow fragment). In further embodiments, the dNTPs comprise one or more labeled nucleotides. In yet a further embodiment, the one or more labeled nucleotides are biotin labeled nucleotides. In still a further embodiment, the extended polynucleotides can be isolated and purified by using a biotin-streptavidin based system. In another embodiment of any of the foregoing embodiments, if the globs assigned to the same barcode span a fraction x of the genome, wherein x<1, then $xe^{-x}$ of the genome will be singly covered, and $1-(x+1)e^{-x}$ of the genome will be multiply covered. In a further embodiment, the polynucleotides are around 500 kilobases in length and more than 5,000 globs are bound to each sector. In still a further embodiment, the polynucleotides are around 50 kilobases in length and more than 50,000 globs are bound to each sector. In yet a further embodiment of any of the foregoing embodiments, the method further comprises sequencing the barcoded polynucleotide fragments. In a further embodiment, the sequences of the barcoded polynucleotides are bioinformatically parsed by extracting the polynucleotide sequences from each glob.

The disclosure also provides a method of determining linkage in genome, comprising assembling and ordering the polynucleotide fragment sequences obtain from the foregoing method comprising the same barcode sequence.

The disclosure also provides a method of determining haplotypes, by sampling the polynucleotide fragment sequences obtained from the foregoing method for sequence variants by comparing the sequences that comprise the same barcode sequence.

The disclosure provides a method to label polynucleotide fragments with a barcode, comprising cross-linking one or more polynucleotides with chromatin or reconstituted chromatin in order to form one or more polynucleotide-polypeptide globs; generating a plurality of sticky ends from digesting the one or more globs with one or more restriction enzymes; contacting the one or more restriction digested globs with one or more sectors of a barcoded oligonucleotide array, wherein the oligonucleotides of the array comprise a nucleotide sequence for a sequencing primer, unique barcode sequence for each sector, and a short sticky end adapter sequence; annealing the sticky ends of one or more restriction digested globs with complementary sticky end adapter sequences of the oligonucleotide array; ligating one strand of each annealed genomic DNA to the array probe; removing the unligated DNA and protein components such that only ligated products, covalently attached to the array remain; polymerizing a second-strand product using the primer sequence common to all array oligos such that the second strand product contain the barcode and the ligated genomic fragment; and recovering the free second-strand product from the array and converting this to a standard sequencing library suitable for high-throughput sequencing and analysis.

The disclosure also provides A method of tagging internal regions of an original nucleic acid molecule, comprising binding the original nucleic acid molecule to at least one polypeptide; cleaving the original nucleic acid to generate at least one double-strand break comprising a first internal free end and a second internal free end; ligating an oligonucleotide tag to at least a first internal free end; separating the oligo-ligated first internal free end from the at least one polypeptide; and sequencing the nucleic acid molecule at a region immediately adjacent to the at least one oligo-ligated first internal free end. In one embodiment, the method comprises crosslinking the original nucleic acid to the at least one polypeptide. In another embodiment, the at least one polypeptide is a nucleic acid binding protein. In still another embodiment, the at least one polypeptide is a nuclear protein. In another embodiment, the at least one polypeptide is a chromatin constituent. In yet another embodiment of any of the foregoing binding the original nucleic acid molecule to at least one polypeptide forms a complex that binds a first segment of the original nucleic acid molecule to a second segment of the original nucleic acid molecule independent of a phosphodiester linkage between the first segment and the second segment. In another embodiment of any of the foregoing, the oligonucleotide tag comprises a sequence that identifies the region immediately adjacent to the at least one oligo-ligated first internal free end as corresponding to the original nucleic acid molecule. In another embodiment of any of the foregoing, cleaving the original nucleic acid to generate at least one double-strand break comprising a first internal free end and a second internal free end comprises contacting the original nucleic acid with a restriction endonuclease. In a further embodiment, the restriction endonuclease is a 6-base cutter. In another embodiment, the restriction endonuclease is a 4-base cutter. In one embodiment, the restriction endonuclease is MboI. In another embodiment of any of the foregoing, cleaving the original nucleic acid to generate at least one double-strand break comprising a first internal free end and a second internal free end comprises contacting the original nucleic acid with a reagent having endonuclease activity. In one embodiment, the reagent is an enzyme. In another embodiment, the endonuclease activity is nonspecific endonuclease activity. In yet another embodiment, the endonuclease activity is specific endonuclease activity.

The disclosure also provides a system for determining genomic phase information in an individual comprising: (a) obtaining a sample from the individual; (b) extracting at least one nucleic acid from the sample; (c) endonucleolytically cleaving the at least one nucleic acid; (d) tagging a first and a second free double-stranded end of the at least one nucleic acid using molecule-specific oligo tags; (e) sequencing the tags and adjacent nucleic acid sequence of the first and second free-double-stranded ends; (f) mapping the end-adjacent sequence of the first and second free double-stranded ends to a nucleic acid sequence data set comprising at least a first sequence read and a second sequence read; (g) assigning the a first sequence read and a second sequence read to a single physical molecule if the first free double-stranded sequence uniquely maps to a first sequence read and the second free double-stranded sequence uniquely maps to a second sequence read, thereby determining genomic phase information in the individual; and (h) providing the genomic phase information to the individual. In one embodiment, the extracting at least one nucleic acid comprises preserving nucleic acid chromatin binding. In another embodiment, the extracting at least one nucleic acid comprises isolating a free nucleic acid molecule. In another embodiment of any of the foregoing the system comprises binding the nucleic acid to at least one polypeptide. In another embodiment of any of the foregoing, the system comprises crosslinking the nucleic acid to at least one polypeptide prior to endonucleolytically cleaving the at least one nucleic acid. In another embodiment of any of the foregoing, the endonucleolytically cleaving the at least one nucleic acid comprises non-enzymatic nucleic acid-cleaving chemical treatment. In still another embodiment of any of the foregoing the endonucleolytically cleaving the at least one nucleic acid comprises treatment with an enzyme having endonuclease activity. In a further embodiment, the enzyme having endonuclease activity is a restriction endonuclease. In still another embodiment, the enzyme having endonuclease activity has nonspecific endonuclease activity. In another embodiment of any of the foregoing, the tagging the first and a second free double-stranded end of the at least one nucleic acid using molecule-specific oligo tags comprises contacting the at least one nucleic acid to an array comprising a plurality of loci, each of said plurality of loci having a tagging oligonucleotide population fixed thereto. In a further embodiment, at least one oligo of at least one tagged oligonucleotide population is fixed to the array at its 3' end. In another embodiment of any of the foregoing, tagging comprises ligating at least one free double-stranded end to at least one oligo. In another embodiment of any of the foregoing, sequencing comprises affixing adapters on either side of a free double-strand break-oligo tag junction. In a further embodiment, affixing adapters comprises polymerase chain reaction amplification. In another embodiment of any of the foregoing, mapping the end-adjacent sequence comprises performing a basic local alignment search of a nucleic acid data set using the end adjacent sequence as a sequence query. In another embodiment of any of the foregoing, providing the genomic phase information to the individual comprises generating a physical copy of an output report. In another embodiment of any of the foregoing, providing the genomic phase information to the individual comprises transmitting an electronically encoded report to the individual. In another embodiment of any of the foregoing, providing the genomic phase information to the individual comprises providing the genomic phase information to a health care professional.

DESCRIPTION OF DRAWINGS

A better understanding of the features and advantages of the disclosure will be obtained by reference to the following detailed description that sets forth illustrative embodiments, in which the principles of the invention are utilized, and the accompanying drawings of which.

DETAILED DESCRIPTION

Figure 1A:
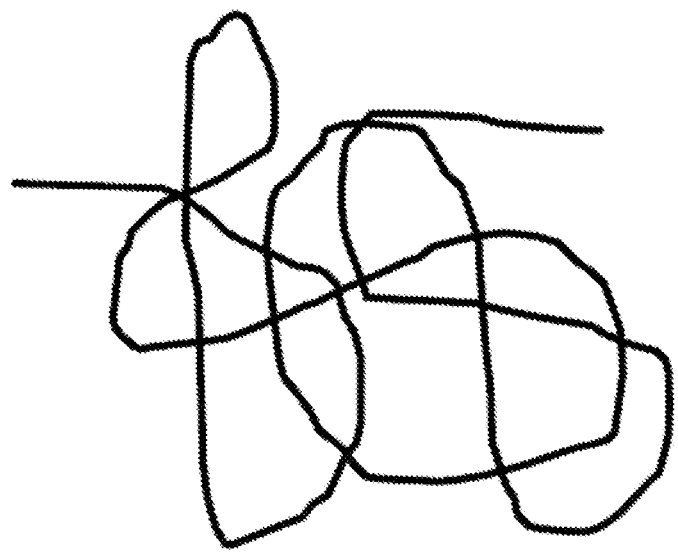
FIGS. 1A-B diagrams the formation of an exemplary class of nucleic acid/protein "glob" complexes by crosslinking double stranded DNA bound to chromatin constituents, and digesting the glob with restriction enzymes. (A) Shows a diagrams a cross-linked "glob" of double-stranded DNA (line), cross-linked to chromatin or reconstituted chromatin or other interacting proteins (not shown). (B) Shows diagrams a 'Glob' that is digested with restriction enzyme (boxes), leading to the formation of numerous sticky ends internal to the input molecule. The glob retains its integrity due to numerous cross-links (not shown) that redundantly bind the nucleic acid molecule's constituent fragments even if the nucleic acid's phosphodiester backbone is cleaved.

As used herein and in the appended claims, the singular forms "a," "and," and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

Unless defined otherwise, all technical and scientific terms used herein have the same meaning as commonly understood to one of ordinary skill in the art. Although there may be many methods and reagents similar or equivalent to those described herein, the exemplary methods and materials are presented herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

The methods, kits and compositions disclosed herein can provide advances in structural and phasing analyses for medical purposes. There is astounding heterogeneity among cancers, individuals with the same type of cancer, or even within the same tumor. Teasing out the causative from consequential effects requires very high precision and throughput at a low per-sample cost. In the domain of personalized medicine, one of the gold standards of genomic care is a sequenced genome with all variants thoroughly characterized and phased, including large and small structural rearrangements and novel mutations. To achieve this with previous technologies demands effort akin to that required for a de novo assembly, which is currently too expensive and laborious to be a routine medical procedure. The methods disclosed herein can rapidly produce complete, accurate genomes at low cost and can thereby yield many highly sought capabilities in the study and treatment of human disease.

The term "contig" as used herein refers to a contiguous nucleic acid sequence that is generated by the assembly of overlapping sequence reads from a given nucleic acid sample. A contig can comprise as few as two overlapping reads or as much overlapping reads to encompass an entire chromosome sequence.

The term "dNTPs" as used herein refer not only to typical nucleotides (e.g., A, G, C, U and T) but also to labeled nucleotides, such as biotin labeled nucleotides and fluorescently labeled nucleotides.

The term "globs" as used herein is in reference to compact polypeptide-nucleic acid complexes comprising one or more nucleic acids that have been bound by a polypeptide or polypeptides to from a redundantly bound complex such that cleavage of phosphodiester backbone bonds of the nucleic acid does not immediately result in loss of nucleic acid physical linkage or phase information. In exemplary embodiments, globs comprise nucleic acids that are reversibly cross-linked to polypeptides, such as histones or other nucleic acid binding molecules.

The term "labeled nucleotide" as used herein refers to a nucleotide that further comprises a molecule capable of detection, including but not limited to radioactive isotopes, fluorophores, chemoluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof that is capable of exhibiting fluorescence in a detectable image. As a consequence the wording and "labeling signal" as used herein indicates the signal emitted from the label that allows detection of the label, including but not limited to radioactivity, fluorescence, chemoluminescence, production of a compound in outcome of an enzymatic reaction and the like.

As used herein, the term "ligating" refers to performing a molecular step or steps that result in a nucleic acid molecule having a continuous sequence defined in part by the terminal sequence of two 'ligated' nucleic acid fragments. The term also refers to attaching oligonucleotides or barcodes to DNA segments. There are a number of different ways of attaching these barcodes to oligonucleotides on an array. For example, physically partitioning DNA/protein globs, and ligating the barcodes would accomplish the same thing. Methods of ligation will be known to those of skill in the art and are described, for example in Sambrook et al. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'->5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation. For a review of ligation based methods see also Conze et al. Annu Rev Anal Chem (2009) 2:215-239.

The term "original nucleic acid" refers to a nucleic acid molecule around which a glob is formed, for example by binding to at least one nucleic acid-binding polypeptide and optionally crosslinking. The term is contrasted with "nucleic acid fragments" or "cleaved nucleic acids" or "exposed internal nucleic acids", or similar terms referring to the novel "subset" nucleic acids formed by cleavage of the original nucleic acid through the methods described herein. Sequence at the borders of these nucleic acid fragments are referred to as "new end adjacent sequence," to contrast with the sequence at the ends of the original nucleic acid.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar, joined to a purine or pyrimidine base and to a phosphate group and that are the basic structural units of nucleic acids. The term "nucleotide analog" refers respectively to a nucleotide in which one or more individual atoms have been replaced with a different atom or with a different functional group. Accordingly, the term polynucleotide includes nucleic acids of any length, including DNA, RNA, and analogs or fragments thereof. A polynucleotide of three or more nucleotides is sometimes referred to as a nucleotidic oligomer or oligonucleotide. A polynucleotide of greater than 100-200 bases is sometimes referred to as a nucleic acid; however, both of the terms "polynucleotide" and "nucleic acid" can be used to refer to nucleotide phosphodiester polymers regardless of length.

The term "reconstituted chromatin" as used herein refers to one or more isolated polynucleotides that have formed complexes with exogenously added nuclear proteins, such as nucleic acid binding proteins in vitro. Examples of approaches to reconstitute chromatin can be found in Lusser et al. ("Strategies for the reconstitution of chromatin," Nature Methods (2004), 1(1):19-26), which is incorporated herein by reference in its entirety, including the references cited therein.

The term "scaffold" as used herein refers to a putative physically linked nucleic acid molecule having a sequence comprising at least two non-overlapping sequence fragments that are nonetheless on a single physically linked molecule. Scaffold sequence can comprise one or more non-overlapping sequence reads or one or more contigs or both contigs and singe sequence reads. The known sequences in a scaffold are often separated by sequence that cannot be uniquely mapped to a single scaffold or that cannot be accurately sequenced, such as repetitive sequence. In some instances, a scaffold corresponds to a putative chromosome sequence, although not all scaffolds correspond to entire chromosomes.

In genome analysis it is useful to identify DNA segments that are close to each other on the same chromosome. For example, by determining which segments are close to each other on the same chromosome allows for: (a) linking sequences together in the reconstruction ("assembly") of a complete genome sequence from fragmentary data; (b) identifying structural variations in an individual relative to a reference genome or as intrinsic heterozygosity in an individual; and (c) properly "phasing" genetic variants that lie on the same chromosome of a homologous pair in a diploid organism (or for phasing polyploids). Such phased variants are referred to as haplotypes. Haplotype information is valuable for proper functional interpretation of compound heterozygote genotypes.

Similarly, in assembling and arranging contigs of sequence such as genomic nucleic acid sequences into higher order arrangements such as 'scaffolds,' learning physical linkage information or phase information is particularly valuable. In particular, physical linkage or phasing information can be used to associate two contigs of non-overlapping sequence to a single scaffold in light of known physical linkage information. Sequences do not need to be physically close to one another in order to be useful for scaffold assembly. Rather, sequences can be physically linked but at opposite ends of a chromosome, for example, and separated by repetitive or difficult to sequence nucleic acid sequence, but can nonetheless be assigned to the same scaffold if physical linkage or phasing data indicates that they are so linked. Determining which segments are physically linked to each other on the same chromosome allows for: (a) linking sequences together in the reconstruction ("assembly") of a complete genome sequence or a scaffold from fragmentary data; (b) identifying structural variations in an individual relative to a reference genome or as intrinsic heterozygosity in an individual; and (c) properly "phasing" genetic variants that lie on the same chromosome of a homologous pair in a diploid organism (or for phasing polyploids). Such phased variants are referred to as haplotypes. Haplotype information is valuable for proper functional interpretation of compound heterozygote genotypes.

In contrast, current methods that provide information of this type are limited. For example, methods directed to paired-end sequencing of a collection of DNA molecules or sequencing junctions of circularized molecules obtained by various means provides collections of read pairs from the same chromosome, a known distance apart, are limited to a specific insert size (primer-pair distance). Single molecule sequencing and/or chromosome capture methods provide only limited information with respect to linkage and phase, and depending on the method may further provide only limited information related to proximity. Shotgun sequencing methods of cloned and pooled fosmid libraries (~40 kb DNA inserts that are captured in a vector and propagated through a bacterial host) while providing information about localization and phase that is distributed across the cloned insert, is susceptible to artifacts generated during processing (e.g., DNA shearing).

The methods disclosed herein, take advantage of the ability to bind a polypeptide or polypeptide population to a nucleic acid so as to redundantly secure the nucleic acid in place in a single glob even if phosphodiester bonds between subsections of the nucleic acid are broken so as, for example, to make the newly exposed internal 'end's at phosphodiester breakpoints available for oligo-tagging. In some embodiments the binding of a polypeptide or polypeptide population to a nucleic acid comprises (reversibly) cross-linking chromatin or other protein-DNA complexes in a way that physically connects different parts of a long DNA molecule through chemical linkages (e.g., see FIG. 1A-B). In some embodiments the globs are formed by nucleic acid-polypeptide complexes in the absence of crosslinking. When, for example, cross-linked protein-DNA complexes are formed, they behave as a single glob unit and can be manipulated without fear that shearing the DNA or otherwise breaking phosphodiester bonds within the nucleic acid constituent of the glob may result in loss of physical linkage information, since the nucleic acid is redundantly bound among its substituent segments by the polypeptide binding agent. The nucleic acid can also be more easily manipulated, because it is in a compact form and is less vulnerable to shearing under normal nucleic acid manipulation.

High molecular weight DNA (>40 kb) can be readily purified and DNA molecules up to ~1 megabase in size can be produced by various existing methods. Reconstituted chromatin can be produced in vitro using available kits or other established protocols. Nucleic acid-polypeptide complexes can similarly be formed using techniques known in the art.

Combining DNA purification with reconstituting chromatin in vitro, isolating chromatin, or binding a nucleic acid with a nucleic acid binding polypeptide or polypeptide population produces a solution of globs that can be manipulated in various ways. For example, DNA which is accessible within glob(s) can be cleaved to generate numerous free DNA ends by using restriction digestion or other cutting means (e.g., see FIG. 1B). For example, with a 4-cutter enzyme, ~1 cut every 256 bp can be produced; with a 5-cutter ~1 cut every ~1,000 bp is produced; with a 6-cutter, ~1 cut every 4,000 bp is produced, etc. Alternatively, bound nucleic acids are cleaved by a nonspecific nucleic acid cutter to produce double-stranded breaks to which an oligo can be ligated or otherwise bound. A non-limiting set of examples of polypeptides that can bind nucleic acids include chromatin constituents, nuclear proteins, transcription factors, nucleic acid repair proteins, transposases, DNA methyltransferases, DNA repair enzymes, proteins comprising inactivated DNA cleaving enzymes that retains DNA binding activity but do not cleave DNA, eubacterial DNA binding enzymes, archaeal DNA binding enzymes, organellar nucleic acid binding proteins or viral DNA binding proteins. In some cases the proteins/polypeptides are chemically treated or genetically modified to limit their native activity (e.g., to eliminate DNA cleaving activity) yet retain the ability to bind double-stranded nucleic acids.

In one embodiment the method includes covalently tagging the resulting exposed double-strand breaks with oligonucleotide barcodes. In some cases, the exposed ends derived from one glob are all covalently bound to a single oligonucleotide population sharing the same barcode and in the simplest form, different globs have different barcodes. Alternatively, in some embodiments multiple globs can share the same oligonucleotide tag, or single globs or single original nucleic acid molecules can be tagged by more than one oligonucleotide population. When the barcoded nucleic acid (e.g., DNA) is sequenced using any number of methods known in the art, the resulting sequences can be bioinformatically parsed, and the DNA sequence derived from each glob extracted. Oligonucleotide tag sequence is correlated with adjacent nucleic acid sequence, and the resulting information is used to assign physical linkage or phase information to the nucleic acid sequence generated. In some embodiments, sequences with the same barcode are by design derived from the same input nucleic acid molecule and are therefore (1) linked on the genome (e.g., up to the size of the original input DNA molecule), and (2) from the same haplotype and so provide the phase of any sequence variants that are sampled by the fragments.

In some embodiments, there is not a 1 to 1 correlation between nucleic acid-polypeptide globs and oligonucleotide tags—that is, some globs are tagged by more than one sequence of oligonucleotide, while some oligonucleotide sequences are bound to more than one glob. In some embodiments, provided that similarly tagged nucleic acid-polypeptide globs do not overlap in sequence, sharing a common oligonucleotide tag does not substantially complicate assembly. In some embodiments, tagging a single glob with oligos having a plurality of sequences does not substantially complicate assembly because, for example, the resulting tagged fragment nucleic acids all map as a comingled population to a common set of contigs or sequence reads.

In direct contrast to end-sequencing or mate-pair methods, multiple sequences from within the input nucleic acid (e.g., DNA) are determined in the same process. Accordingly, particularly for long nucleic acids, physical linkage or phase information is obtained not only for the end-paired sequence but for a number of 'new end' adjacent sequences generated by the cleavage of the nucleic acid to expose internal double-strand breaks.

These new end adjacent sequences will predominantly be adjacent to a sequence that is internal to the original nucleic acid molecule. By determining the sequence adjacent to the free nucleic acid ends of the glob, one can infer that contigs or individual sequence reads to which the cleavage-adjacent sequence maps correspond to a single scaffold and are physically linked on a single molecule. Thus in end-sequencing only the contigs or sequence reads to which the end sequences of a nucleic acid molecule are mapped can be placed on a common scaffold; but according to the methods, systems and compositions disclosed herein 'new end adjacent sequences' are generated throughout the original nucleic acid molecule, such that in some embodiments, all or a substantial number of contigs or sequence reads spanned by an original nucleic acid molecule are identified and can be assigned to a common phase or physical linkage group.

In additional methods disclosed herein, collections of globs that together represent a modest fraction x (<1) of the genome can be assigned to the same barcode. In this case, sequences with the same barcode are no longer necessarily derived from the same input DNA molecule. Nevertheless, if the globs assigned to the same barcode span a fraction x of the input genome then $xe^{-x}$ of the genome will be singly covered and only $1-(x+1)e^{-x}$ of the genome will be multiply covered. In multiply covered regions, phase may be ill-defined if both haplotypes are sampled. For example, if x=0.5, then 30% of the genome is singly covered by globs and 9% of the genome is doubly covered. ~4% will be double covered by the same haplotype, and can be phased with suitable bionformatic tools. By suitable choice of x, various regimes can be realized.

Figure 2:
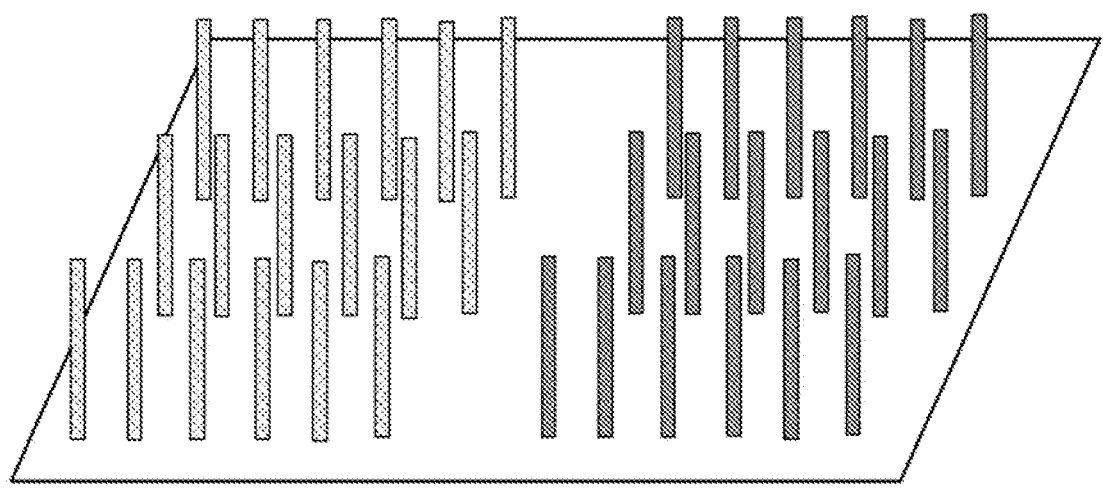
FIG. 2 diagrams an oligonucleotide barcode array. An oligonucleotide array is produced with thousands to greater than one million sectors.

In certain embodiments, methods disclosed herein comprise a step of constructing a barcoded oligonucleotide array. An oligonucleotide array can be constructed so that different sectors of the array contain different sequences (barcodes) (e.g., see FIG. 2). Such arrays are commercially available with user-defined oligonucleotide sequences. For example, custom barcoded oligonucleotide array can be purchased from at least the following companies: Affymetrix, Agilent, MYcroarray, CustomArray, Arrayit, and Akoni Biosystems. The oligonucleotide of the barcoded array comprises: (1) sequencing primer at the attached end; (2) unique barcodes for each sector; and (3) short sticky-end adapter sequences at their free ends. Based on current oligonucleotide array technology, it is expected that there will be >~1 million sectors, each ~100 microns across. Each sector bears millions of copies of a sector-specific barcode.

The barcoded oligonucleotide arrays can be constructed using a variety of technologies, including printing with fine-pointed pins onto glass slides, photolithography using pre-made masks, photolithography using dynamic micro-mirror devices, ink-jet printing, or electrochemistry on microelectrode arrays. Such arrays are commercially available. These arrays are made, for example, by synthesizing oligonucleotide probes having a sequence comprising a sequencing primer at the attached end, a unique barcode for each sector, and short sticky-end adapter sequences. The probes are then deposited on the array surface and are then "spotted" onto glass. A common approach utilizes an array of fine pins or needles controlled by a robotic arm that is dipped into wells containing the probes and then depositing each the probes at designated locations on the array surface. The resulting "grid" therefore provides for thousands to millions of copies of oligonucleotide probes comprising unique barcodes for each sector and it would be expected that the grid can contain hundreds to millions of sectors. The barcoded oligonucleotide arrays are then ready to receive complementary sticky ends from restriction-digested globs. The arrays may be easily customized for each experiment, by choosing the probes and printing locations on the arrays.

Alternatively, barcoded oligonucleotide arrays can be produced by printing short oligonucleotide sequences comprising a sequencing primer at the attached end, a unique barcode for each sector, and short sticky-end adapter sequence directly onto the array surface instead of depositing intact sequences. One technique used to produce oligonucleotide arrays includes photolithographic synthesis (e.g., see U.S. Pub. No. 20090036324) on a silica substrate where light and light-sensitive masking agents are used to "build" a sequence one nucleotide at a time across a portion or the entire array. Bathing the array in a solution of a single nucleotide, then a masking reaction takes place and the next set of probes are unmasked in preparation for a different nucleotide exposure. After many repetitions, the sequences of oligonucleotide probes comprising unique barcodes for each sector can be constructed. More recently, Maskless Array Synthesis from NimbleGen Systems has combined flexibility with large numbers of probes.

Figure 1B:
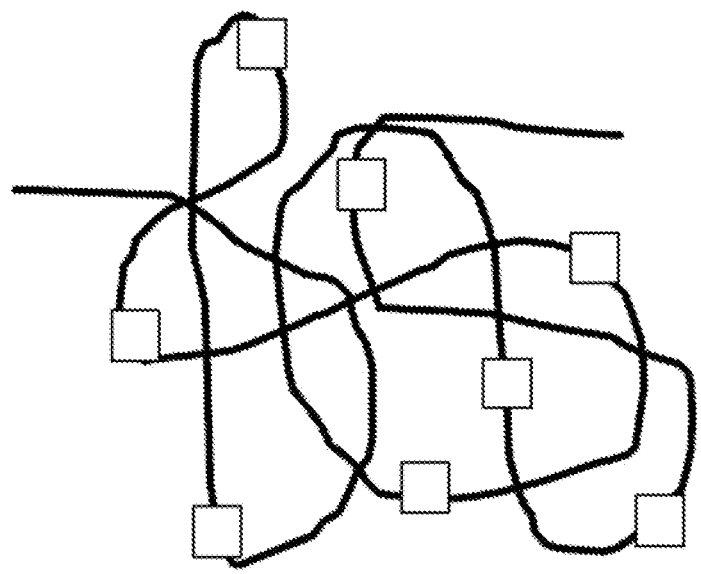

In particular embodiments, methods disclosed herein comprise a step of: cross-linking one or more polynucleotides with chromatin or reconstituted chromatin to form one or more polypeptide/protein-nucleic acid globs (e.g., see FIG. 1A). In certain embodiments the methods disclosed herein utilize chromatin that has been formed within a cell/organism, such as chromatin isolated from cultured cells or primary tissue, that can be used to crosslink one or more polynucleotides. In alternate embodiments, the methods disclosed herein utilize reconstituted chromatin formed in vitro. In alternate embodiments, the methods disclosed herein utilize nucleic acid/polypeptide complexes that comprise nucleic acid binding proteins other than chromatin constituents, such as other nuclear polypeptides or other nucleic acid binding proteins.

Reconstituted chromatin or nonchromatin nucleic acid-polypeptide complexes assembled in vitro have many benefits over chromatin formed within a cell/organism. First, for many samples, the collection of naked DNA samples can be achieved by using a variety of noninvasive to invasive methods, such as by collecting bodily fluids, swabbing buccal or rectal areas, taking epithelial samples, etc. For example, naked DNA is relatively easy to isolate compared to intact chromatin, which may require that substantially more precautions be taken to maintain its integrity. Moreover, it may be impractical to successfully culture certain types of cells long-term. Second, reconstituted chromatin will not have the inter-chromosomal and other long-range interactions that generate artifacts for genome assembly and haplotype phasing. Third, by varying the ratio of DNA to histones, it is possible to reduce the nucleosome density. In this way, crosslinks will naturally favor longer-range interactions.

Crosslinking of chromatin or reconstituted chromatin proteins (such as histones) or other nucleic acid binding proteins to the one or more polynucleotides or nucleic acids to form globs can be accomplished according to various methods. One approach is to expose the chromatin to ultraviolet irradiation (Gilmour et al., *Proc. Nat'l. Acad. Sci. USA* 81:4275-4279 (1984)). Other approaches utilize chemical crosslinking agents. Suitable chemical crosslinking agents include, but are not limited to, formaldehyde and psoralen (Solomon et al., *Proc. Natl. Acad. Sci. USA* 82:6470-6474 (1985); Solomon et al., *Cell* 53:937-947

(1988)). The one or more polynucleotides may be purified by immunoprecipitation prior to or after crosslinking. Such methods generally involve contacting the cross-linked polynucleotide(s) with an antibody, for example, that specifically recognizes and binds to acetylated histones, such as H3. Examples of such antibodies include, but are not limited to, Anti Acetylated Histone H3, available from Upstate Biotechnology, Lake Placid, N.Y. However, any antibody that binds to histones can work. The globs can subsequently be recovered from the immunoprecipitate.

As an alternative, globs can be formed in the absence of crosslinking provided that the polypeptides are sufficiently tightly bound to the nucleic acids that the globs maintain their integrity during any manipulation related to, for example, endonuclease-activity mediated cleavage of the bound nucleic acid.

High molecular weight DNA (>40 kb) can be readily purified and DNA molecules up to ~1 megabase in size can be produced by various existing methods. For example, very high molecular weight DNA can be extracted by very gentle cell lysis (Teague et al., *Proc. Nat. Acad. Sci. USA* 107(24): 10848-53 (2010)) and agarose plugs (Schwartz, D. C., & Cantor, C. R., *Cell* 37(1):67-75 (1984)). In other cases, commercially available machines that can purify DNA molecules up to megabases in length can be used to extract very high molecular weight DNA.

In particular embodiments, methods disclosed herein comprise generating a plurality of sticky ends from cleaving a bound nucleic acid constituent of a nucleic acid-polypeptide glob with an enzyme demonstrating endonuclease activity. In some cases, the enzyme is selected from one or more restriction enzymes known in the art, wherein the sticky ends generated comprise an overhang compatible with a sticky-end adapter sequences on a barcoded oligonucleotide array (e.g., see FIG. 1B). Accordingly the sticky ends and sticky-end adapter sequences can be designed to have particular sequences based upon the particular restriction site for a selected restriction enzyme. It should be understood that the choice of the particular restriction enzyme may be based on variety considerations, including how often the restriction enzyme may cut any stretch of a polynucleotide, the length of the sticky end, commercial availability, cost, and efficiency of the enzyme. As there are over 3000 restriction enzymes that have been studied in detail, and more than 600 of these which are commercially available, there is a large selection of enzymes which can be used in the methods disclosed herein.

Figure 3:
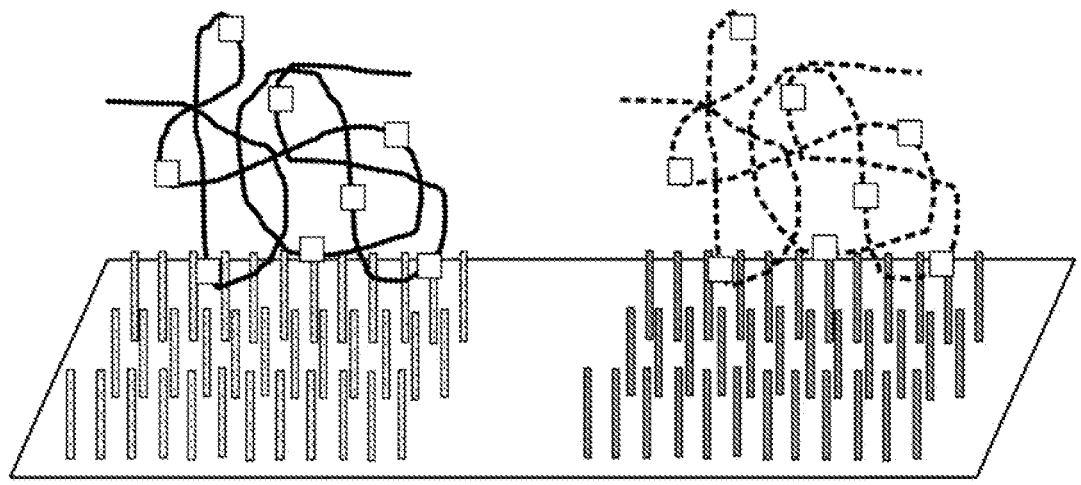
FIG. 3 diagrams digested globs that are applied to the array. Here the boxes represent locations where DNA has been cut and sticky ends are found.

In certain embodiments, methods disclosed herein comprise a step of: applying the digested globs to the barcoded oligonucleotide array in such a manner that each sector binds globs that collectively cover a fraction x of the genome, where x<1. If the DNA inputs are ~500 kilobases, then 1× coverage of a human genome is ~6000 globs. If the DNA inputs are a more modest 50 kb (comparable in scale to a fosmid library) then 60,000 globs can be bound to each sector. Globs representing different regions of the genome will fall on different sectors of the array, and will stick to, and eventually be covalently labeled by the corresponding sector-specific code (e.g., see FIG. 3).

In particular embodiments, methods disclosed herein comprise a step of: annealing the sticky ends of the digested globs to the surface of the array by Watson-Crick pairing the sticky ends of the globs with complementary sticky-end adapter sequences. If these sticky ends are ligated together, the glob will become covalently linked to the array oligonucleotides at numerous positions.

In alternate embodiments, sticky ends as generated above are annealed to oligo adapters in solution, for example in wells of a multi-well plate into which a liquid comprising a plurality of globs has been aliquoted. In some embodiments, the globs are diluted to a final concentration of one or about one glob per well. In some embodiments, the globs are adjusted to a final concentration of greater than one glob per well. In some cases, the endonuclease cleavage generates blunt rather than sticky ends, and the oligo adapters are added, for example, via blunt end ligation or other annealing-independent ligation process.

In some embodiments, methods disclosed herein comprise a step of: extending the sequence of the array-bound oligonucleotide into the glob and the globs into the oligonucleotide using strand-displacing DNA polymerase and dNTPs. Examples of strand-displacing DNA polymerases include, but not limited to, phi29, Bst DNA Polymerase (large fragment), Bsu DNA Polymerase (large fragment), Deep VentR™ DNA Polymerase, Deep VentR™ (exo-)DNA Polymerase, and DNA Polymerase I (Klenow fragment). The resulting extended polynucleotides comprise a sequencing primer, sector barcode, annealed sticky ends, and polynucleotides from the glob. The glob polynucleotide fragments come from throughout the glob, and therefore represent distinct segments of the original input polynucleotides (e.g., see FIG. 4). The extended polynucleotide can be cleaved from the array releasing barcoded DNA fragments. Capture of the barcoded DNA fragments is facilitated by including biotinylated dNTPs in the polynucleotide extension mixture.

In some embodiments, 'new ends' are tagged by addition of an oligo or population of oligos to at least some new ends of a glob. Globs are then disassembled and tagged new fragments are sequenced. Prior to sequencing, in some cases the tagged new fragments are further tagged by PCR mediated amplification, introducing a second set of tags and introducing sequencing primers to the ends of the new tagged fragments. In some cases, prior to glob disassembly, exposed nucleic acid segments are sheared or cleaved from the glob and collected for sequencing. In some cases sheared or cleaved exposed nucleic acid segments are further tagged by PCR mediated amplification, introducing a second set of tags and introducing sequencing primers to the ends of the new tagged fragments.

Figure 5:
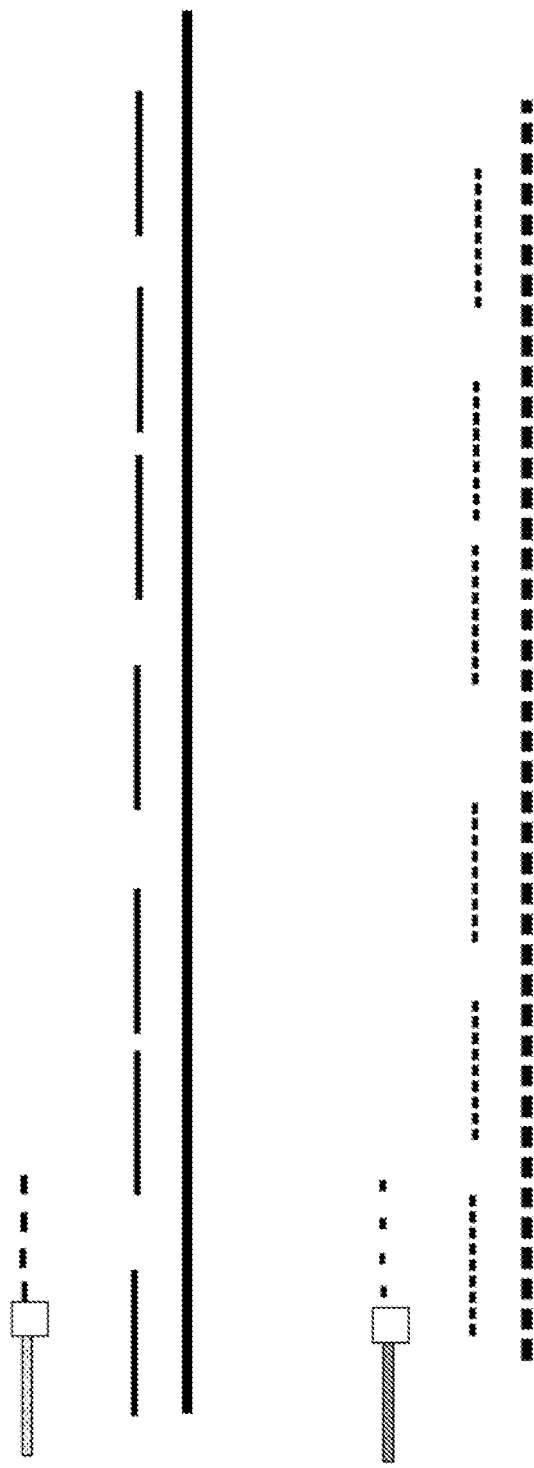
FIG. 5 diagrams that the location of each read on the array can be inferred from its barcode. Reads that originate from the same glob necessarily contain the same array barcode.

The barcoded DNA can then be sequenced using any number of methods known in the art, the resulting sequences can be bioinformatically parsed, and the DNA sequence derived from each glob extracted (e.g., see FIG. 5). If a reference genome is present, the reads can be aligned to the reference, allowing phasing of variants to be accomplished and contigs to be assembled into scaffolds, and structural variants to be recognized based on the disposition of the aligned reads. In the absence of a reference, the reads with the same barcode are a priori more likely to be close to one another (i.e., within the size of the original input DNA) and their distribution can be predicted theoretically.

Upon sequencing, the (known) barcodes can be identified bioinformatically. These can be designed to enable "error correction" by ensuring that no two sectors have barcodes that are within a single nucleotide change of each other. It may also be useful to ensure uniform melting temperatures and other physicochemical properties of the oligos/barcodes. The sequences that are attached to each barcode represent sequence of the original input polynucleotide (e.g., see FIG. 5).

FIGS. 6A-G depict an array- and restriction-endonuclease-based embodiment of the disclosure herein.

Figure 6A:
FIG. 6A-G shows a more detailed step-by-step process of an embodiment of the disclosure. (A) Depicts the structure of oligonucleotides comprising barcodes. The linker, primer and sticky-end complement sequence are typically the same for all array features (spots or loci), while the barcode differs and in some embodiments is unique. (B) Shows double-stranded DNA, in covalently linked globs in some embodiments, with single-stranded overhangs is hybridized to the surface of an array. Some free sticky ends hybridize to the array oligos because they have compatible overhangs. (C) Shows one strand of the DNA is ligated to the array probe wherein the hybridization has occurred. In the embodiment depicted herein, one strand of the genomic DNA is now covalently linked to the array. The other strand is not. (D) Shows the unligated strands and all protein components are removed via high temperature incubation in a mild detergent solution. Ligated, single-stranded products remain as they are covalently linked to the array probes. (E) Shows a primer oligo complementary to the array primer sequence is hybridized to the array. (F) Shows a polymerase (not shown) and dNTPs are added for second strand synthesis. Note that second strand products are generated from array oligos that had genomic DNA ligated and from those that did not. Labeled dNTPs can be added to assist purification of the second-strand product. The second strand product is not covalently attached to the array in some embodiments. (G) Shows a second strand product is collected from the array by simple heat treatment. It can be further purified using the biotin or other label added to the second strand synthesis mixture. This is then converted into a sequencing library.

As elsewhere described herein, array oligos comprise the four parts indicated in FIG. 6A. The linker, primer and sticky-end complement sequence is the same for all array features (spots or loci) in some embodiments, while the barcode differs and in some embodiments is unique to each spot. The linker sequence simply provides space for the primer sequence to be tethered from but separate from the array surface. In some embodiments its sequence may vary without affecting practice of the methods herein. The sticky end complement is designed to be compatible with sticky end overhangs of DNA globs in some embodiments.

Figure 6B:
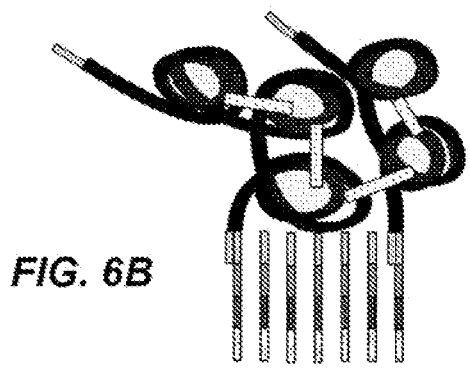

In FIG. 6B, double-stranded DNA, in covalently linked globs in some embodiments, with single-stranded overhangs is hybridized to the surface of an array. Some free sticky ends hybridize to the array oligos because they have compatible overhangs.

Figure 6C:
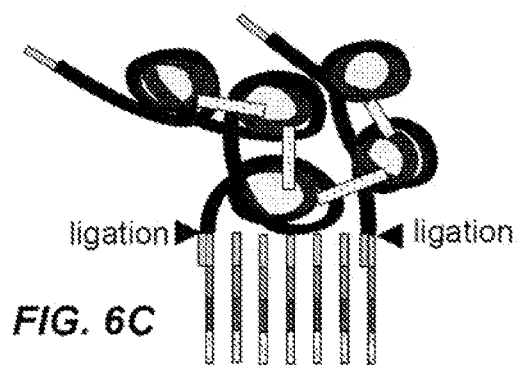

In FIG. 6C, one strand of the DNA is ligated to the array probe wherein the hybridization has occurred. In the embodiment depicted herein, one strand of the genomic DNA is now covalently linked to the array. The other strand is not.

Figure 6D:
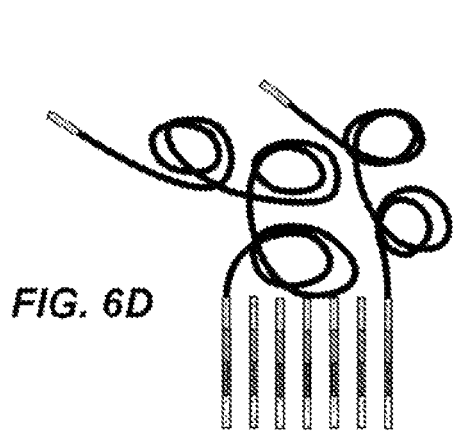

In FIG. 6D, the unligated strands and all protein components are removed via high temperature incubation in a mild detergent solution. Only ligated, single-stranded products remain as they are covalently linked to the array probes.

Figure 6E:
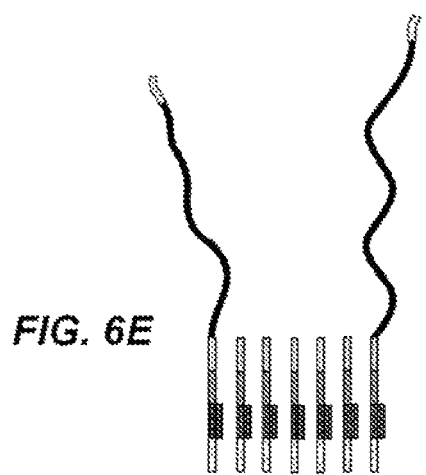

In FIG. 6E, a primer oligo complementary to the array primer sequence is hybridized to the array.

Figure 6F:
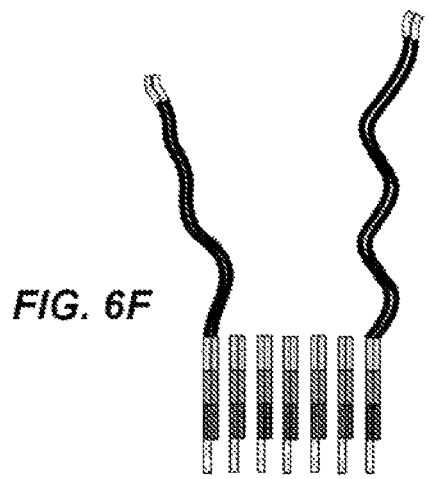

In FIG. 6F, a polymerase (not shown) and dNTPs are added for second strand synthesis. Note that second strand products are generated from array oligos that had genomic DNA ligated and from those that did not. Labeled dNTPs can be added to assist purification of the second-strand product. The second strand product is not covalently attached to the array in some embodiments.

Figure 6G:
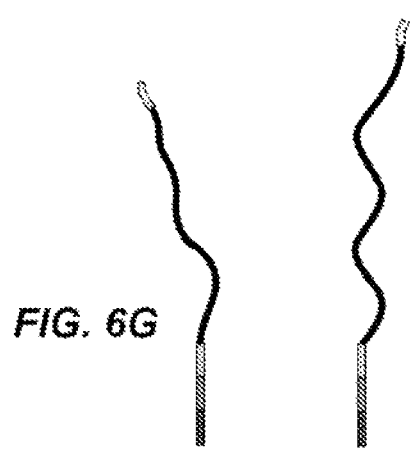

In FIG. 6G, second strand product is collected from the array by simple heat treatment. It can be further purified using the biotin or other label added to the second strand synthesis mixture. This is then converted into a sequencing library. In some embodiments products contain the barcode denoting its home array spot and all the products of the same source DNA glob will have the same barcode.

The use of globs to manipulate large DNA molecules has additional applications. For example, nucleic acid globs are used to capture specific sequences of biomedical interest (e.g., the HLA region) using antisense probes. The advantage of using globs rather than free DNA is that larger pieces are captured and manipulated with substantially less risk of shearing the nucleic acid molecules disturbing their integrity. These sequences would then be amplified for targeted sequencing of specific DNA regions.

The methods disclosed herein can be used to label and/or associate polynucleotides or sequence segments thereof, and to utilize that data for various applications. In some cases, the disclosure provides methods that can produce a highly contiguous and accurate human genomic assembly with less than about 10,000, about 20,000, about 50,000, about 100,000, about 200,000, about 500,000, about 1 million, about 2 million, about 5 million, about 10 million, about 20 million, about 30 million, about 40 million, about 50 million, about 60 million, about 70 million, about 80 million, about 90 million, about 100 million, about 200 million, about 300 million, about 400 million, about 500 million, about 600 million, about 700 million, about 800 million, about 900 million, or about 1 billion read pairs. In some cases, the disclosure provides methods that phase, or assign physical linkage information to, about 50%, 60%, 70%, 75%, 80%, 85%, 90%, 91%, 92%, 93%, 94%, 95%, 96%, 97%, 98%, 99% or more of heterozygous variants in a human genome with about 50%, 60%, 70%, 75%, 80%, 85%, 90%, 91%, 92%, 93%, 94%, 95%, 96%, 97%, 98%, 99%, or greater accuracy.

Further, the range of the associated sequence segments generated by the disclosure can be extended to span much larger genomic distances. The assembly can be produced from a standard shotgun library in addition to a library of associated sequence segments (i.e. a read-set). The sequence segments can, for example, be associated based on a label. Sequence segments labeled with a common label can be associated to one another, and optionally binned together to form a "read-set". In some cases, the label can be a barcode sequence.

In some cases, the disclosure provides software that can utilize both the standard shotgun library and the read-set. The phased variants can be produced with a single long-range read pair library. The reads can be mapped to a reference genome and used to assign variants to one of the individual's two parental chromosomes. Further, the disclosure provides methods for the extraction of even larger DNA fragments using known techniques, so as to generate exceptionally long reads.

The methods provided herein can greatly advance the field of genomics by overcoming the substantial barriers posed by these repetitive regions and can thereby enable important advances in many domains of genomic analysis. Since the methods described herein can produce very long-range read-sets, de novo assembly can be achieved with a single sequencing run. This may cut assembly costs by orders of magnitude and shorten the time required from months or years to weeks. In some cases, the methods disclosed herein allow for generating a plurality of read-sets in less than 14 days, less than 13 days, less than 12 days, less than 11 days, less than 10 days, less than 9 days, less than 8 days, less than 7 days, less than 6 days, less than 5 days, less than 4 days, less than 3 days, less than 2 days, less than 1 day or in a range between any two of foregoing specified time periods. For example, the methods can allow for generating a plurality of read-sets in about 10 days to 14 days. Building genomes for even the most niche of organisms become routine, phylogenetic analyses may suffer no lack of comparisons, and projects such as Genome 10 k are realized.

The methods described herein allow for assignment of previously provided, previously generated, or de novo synthesized contig information into physical linkage groups such as chromosomes or shorter contiguous nucleic acid molecules. Similarly, the methods disclosed herein allow said contigs to be positioned relative to one another in linear order along a physical nucleic acid molecule. Similarly, the methods disclosed herein allow said contigs to be oriented relative to one another in linear order along a physical nucleic acid molecule.

Further, applying the methods disclosed herein to phasing can combine the convenience of statistical approaches with the accuracy of familial analysis, providing savings—money, labor, and samples—greater than those using either method alone. De novo variant phasing, a highly desirable phasing analysis that is prohibitive with previous technologies, can be performed readily using the methods disclosed herein. This is particularly important as the vast majority of human variation is rare (less than 5% minor allele frequency). Phasing information is valuable for population genetic studies that gain significant advantages from networks of highly connected haplotypes (collections of variants assigned to a single chromosome), relative to unlinked genotypes. Haplotype information can enable higher resolution studies of historical changes in population size, migrations, and exchange between subpopulations, and allows us to trace specific variants back to particular parents and grandparents. This in turn clarifies the genetic transmission of variants associated with disease, and the interplay between variants when brought together in a single individual. The methods of the disclosure can eventually enable the preparation, sequencing, and analysis of extremely long range read-set (XLRS) libraries.

The methods disclosed herein can dramatically simplify de novo genomic assembly for a wide range of organisms. Using previous technologies, such assemblies are currently limited by the short inserts of economical mate-pair libraries. The methods disclosed herein can provide read pairs capable of spanning large distances (e.g., megabases or longer) and thereby overcome these scaffold integrity challenges. Accordingly, producing chromosome-level assemblies can be routine by utilizing the methods disclosed herein. Similarly, the acquisition of long-range phasing information can provide tremendous additional power to population genomic, phylogenetic, and disease studies. The methods disclosed herein can enable accurate phasing for large numbers of individuals, thus extending the breadth and depth of our ability to probe genomes at the population and deep-time levels.

In some cases, a nucleic acid sample is incompletely fragmented such that multiple copies of homologous nucleic acids are fragmented differentially with respect to one another, in some cases resulting in overlapping fragments having identical sequence in their positions of overlap but having non-identical molecular ends. In some cases, molecular tagged sequences that map to each individual molecular fragment, such as overlapping sequence spanning at least one polymorphism that may differ among homologous chromosome pairs. In such cases, by comparing the sequence at the position that may differ among homologous chromosome pairs, one determines whether the overlapping sequences represent sequence from the sample phase that is the same physically linked chromosome or original nucleic acid of the sample.

In some cases, the methods disclosed herein comprise the step of generating a plurality of contigs from sequencing fragments of target DNA obtained from a subject. Long stretches of target DNA can be fragmented by cutting the DNA with one or more restriction enzymes, incompletely digesting the DNA with one or more nonspecific endonucleases, shearing the DNA, or a combination thereof. The resulting fragments can be sequenced using high throughput sequencing methods to obtain a plurality of sequencing reads. Examples of high throughput sequencing methods which can be used with the methods of the disclosure include, but are not limited to, 454 pyrosequencing methods developed Roche Diagnostics, "clusters" sequencing methods developed by Illumina, SOLiD and Ion semiconductor sequencing methods developed by Life Technologies, and DNA nanoball sequencing methods developed by Complete Genomics. Overlapping ends of different sequencing reads can then be assembled to form a contig. Alternatively, fragmented target DNA can be cloned into vectors. Cells or organisms are then transfected with the DNA vectors to form a library. After replicating the transfected cells or organisms, the vectors are isolated and sequenced to generate a plurality of sequencing reads. The overlapping ends of different sequencing reads can then be assembled to form a contig.

Alternately or in combination with the above, the methods disclosed herein may be used with contig information previously generated. Contig information for a vast number of genomes, including the human genome, is publicly available (see, for example, sequence available at the National Center for Biotechnology Information, the Joint Genome Institute, the Eukaryotic Pathogen Database, or any number of species-specific genome web pages). Rather than generating contig information de novo, or in combination with de novo generated contig data, the methods disclosed herein may be used to assist in the chromosomal assembly, ordering and orientation of these previously generated contigs.

The methods disclosed herein can allow for accurate and predictive results for genotype assembly, haplotype phasing, and metagenomics with small amounts of materials. In some cases, less than about 0.1 ug, about 0.2 ug, about 0.3 ug, about 0.4 ug, about 0.5 ug, about 0.6 ug, about 0.7 ug, about 0.8 ug, about 0.9 ug, about 1.0 ug, about 1.2 ug, about 1.4 ug, about 1.6 ug, about 1.8 ug, about 2.0 ug, about 2.5 ug, about 3.0 ug, about 3.5 ug, about 4.0 ug, about 4.5 ug, about 5.0 ug, about 6.0 ug, about 7.0 ug, about 8.0 ug, about 9.0 ug, about 10 ug, about 15 ug, about 20 ug, about 30 ug, about 40 ug, about 50 ug, about 60 ug, about 70 ug, about 80 ug, about 90 ug, about 100 ug, about 150 ug, about 200 ug, about 300 ug, about 400 ug, about 500 ug, about 600 ug, about 700 ug, about 800 ug, about 900 ug, or about 1000 ug of DNA can be used with the methods disclosed herein. In some cases, the DNA used in the methods disclosed herein can be extracted from less than about 1,000,000, about 500,000, about 200,000, about 100,000, about 50,000, about 20,000, about 10,000, about 5,000, about 2,000, about 1,000, about 500, about 200, about 100, about 50, about 20, or about 10 cells.

In some cases, a method to extract very high molecular weight DNA is provided. In some cases, the data from an XLRS library can be improved by increasing the fragment size of the input DNA. In some examples, extracting megabase-sized fragments of DNA from a cell can produce read-sets comprising reads separated by megabases in the genome. In some cases, the read-sets can provide sequence information over a span of greater than about 10 kB, about 50 kB, about 100 kB, about 200 kB, about 500 kB, about 1 Mb, about 2 Mb, about 5 Mb, about 10 Mb, or about 100 Mb. In some examples, the read-sets can provide sequence information over a span of greater than about 500 kB. In further examples, the read-sets can provide sequence information over a span of greater than about 2 Mb. In some cases, the very high molecular weight DNA can be extracted by very gentle cell lysis (Teague, B. et al. (2010) *Proc. Nat. Acad. Sci. USA* 107(24), 10848-53) and agarose plugs (Schwartz, D. C., & Cantor, C. R. (1984) *Cell*, 37(1), 67-75). In other cases, commercially available machines that can purify DNA molecules up to megabases in length can be used to extract very high molecular weight DNA.

The methods disclosed herein can be used with chromatin isolated from a cell/organism, with reconstituted chromatin, or with nucleic acids bound to non-chromatin polypeptides. Reconstituted chromatin or nucleic acid globs formed by non-chromatin nucleic acid binding proteins is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin or forming globs comprising non-chromatin nucleic acid binding proteins substantially prevents the formation of inter-chromosomal and other long-range interactions that generate artifacts for genome assembly and haplotype phasing. In some cases, a sample may have less than about 20, 15, 12, 11, 10, 9, 8, 7, 6, 5, 4, 3, 2, 1, 0.5, 0.4, 0.3, 0.2, 0.1% or less inter-chromosomal or intermolecular crosslinking according to the methods and compositions of the disclosure. In some examples, the sample may have less than about 5% inter-chromosomal or intermolecular crosslinking. In some examples, the sample may have less than about 3% inter-chromosomal or intermolecular crosslinking. In further examples, the sample may have less than about 1% inter-chromosomal or intermolecular crosslinking. Third, the frequency of sites that are capable of crosslinking and thus the frequency of intramolecular crosslinks within the polynucleotide can be adjusted. For example, the ratio of DNA to histones can be varied, such that the nucleosome density can be adjusted to a desired value. In some cases, the nucleosome density is reduced below the physiological level. Accordingly, the distribution of crosslinks can be altered to favor longer-range interactions. In some embodiments, sub-samples with varying cross-linking density may be prepared to cover both short- and long-range associations. For example, the crosslinking conditions can be adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule.

In various cases, the methods disclosed herein can be used to produce read-sets comprising reads that are separated by large distances. The upper limit of this distance may be improved by the ability to collect DNA samples of large size. In some cases, the reads can be separated by up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp or more in genomic distance. In some examples, the reads can be separated by up to 500 kbp in genomic distance. In other examples, the reads can be separated by up to 2000 kbp in genomic distance. The methods disclosed herein can integrate and build upon standard techniques in molecular biology, and are further well-suited for increases in efficiency, specificity, and genomic coverage. In some cases, the read-sets can be generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some examples, the read-sets can be generated in less than about 14 days. In further examples, the read-sets can be generated in less about 10 days. In some cases, the methods of the present disclosure can provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs. For example, the methods can provide about 90 to 100% accuracy in correctly ordering and/or orientating the plurality of contigs.

In some embodiments sequence tag information is used to map sequence reads to a single nucleic acid molecule from which they originated. In some embodiments this information is independent of distance information within a single nucleic acid molecule. In some cases the nucleic acid molecule is obtained from a population of incompletely fragmented or sheared genomic DNA, which is sheared such that overlapping nucleic acid fragments are obtained. Upon sequencing the reads which correspond to each individual overlapping nucleic acid molecule, one may assemble larger 'read position contig' information to infer phase or physical linkage information across distances beyond single sheared nucleic acid size.

The intrachromosomal interactions can be used to correlate chromosomal connectivity. Similarly, the nucleic acid fragment mapping data can be used to correlate chromosomal connectivity. The intrachromosomal data can aid genomic assembly. In some cases, the chromatin can be reconstructed in vitro. This can be advantageous because chromatin—particularly histones, the major protein component of chromatin—is important for DNA fixation. For example, chromatin can form a stable complex with DNA to capture the spatial and sequence information, which may be analyzed to aid genomic assembly. Chromatin is highly non-specific in terms of sequence and can be generally assemble uniformly across the genome. In some cases, the genomes of species that do not use chromatin can be assembled on a reconstructed chromatin and thereby extend the horizon for the disclosure to all domains of life.

In some cases, cross-links can be created between genome regions that are in close physical proximity. Crosslinking of proteins (e.g. histones) to the DNA molecule (e.g. genomic DNA), within chromatin can be accomplished according to a suitable method described in further detail elsewhere herein or otherwise known in the art. In some cases, two or more nucleotide sequences can be cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical cross-linking agents include, but are not limited to, formaldehyde and psoralen (Solomon et al., Proc. Nat. Acad. Sci. USA 82:6470-6474, 1985; Solomon et al., Cell 53:937-947, 1988). For example, cross-linking can be performed by adding a solution comprising about 2% formaldehyde to a mixture comprising the DNA molecule and chromatin proteins. Other examples of agents that can be used to cross-link DNA include, but are not limited to, UV light, mitomycin C, nitrogen mustard, melphalan, 1,3-butadiene diepoxide, cis diaminedichloroplatinum(II) and cyclophosphamide. Suitably, the cross-linking agent will form cross-links that bridge relatively short distances—such as about 2 Å—thereby selecting intimate interactions that can be reversed.

In some cases, the DNA molecule may be immunoprecipitated prior to or after crosslinking. In some cases, the DNA molecule can be fragmented into two or more sequence segments. Sequence segments may be contacted with a binding partner, such as an antibody that specifically recognizes and binds to acetylated histones, e.g., H3. Examples of such antibodies include, but are not limited to, Anti Acetylated Histone H3, available from Upstate Biotechnology, Lake Placid, N.Y. The polynucleotides from the immunoprecipitate can subsequently be collected from the immunoprecipitate. Prior to fragmenting the polynucleotide, the acetylated histones can be cross-linked to adjacent polynucleotide sequences. The mixture can then be treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing, contacting with enzymes or other chemicals having nonspecific endonuclease activity and/or the use of restriction enzymes. The restriction enzyme can have a restriction recognition site of 1, 2, 3, 4, 5, 6, 7, 8, or more than 8 bases long. Examples of restriction enzymes include but are not limited to AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpyl66II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspAlI, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Taqαl, TfiI, TliI, TseI, Tsp45I, Tsp509I, TspMI, TspRI, Tth111I, XbaI, XcmI, XhoI, XmaI, XmnI, and ZraI. The resulting sequence segments can vary in size. The resulting sequence segments may also comprise a single-stranded overhand at the 5' or 3' end.

In some embodiments, using sonication techniques, sequence segments of about 100 to 5000 nucleotides can be obtained. Alternatively, sequence segments of about 100 to 1000, about 150 to 1000, about 150 to 500, about 200 to 500, or about 200 to 400 nucleotides can be obtained.

The sample can be prepared for sequencing the cross-linked sequence segments. In some cases, sequence segments that were intramolecularly cross-linked can be labeled with a common label. The common label can then be detected and analyzed to determine sequence segments that were intramolecularly cross-linked. The common label can, for example, be a barcode, which can optionally be detected by sequencing methods. The reads of sequence segments labeled with a common label can be binned into a read-set.

Sequence information may be obtained from the sample using any suitable sequencing technique described in further detail elsewhere herein or otherwise known in the art, such as a high throughput sequencing method. For example, the sequence segments can be subject to a sequencing technique to generate sequence reads, which can be used to identify sequence segments that are cross-linked and/or are labeled with a common label. Two or more sequence segments can be represented in the obtained sequence information, associating haplotyping information over a linear distance separating the two sequence segments along the polynucleotide.

In some cases, the methods disclosed herein are used in combination with an existing sequencing technology. In some cases, the methods disclosed herein are used with technologies and approaches derived from any existing sequencing technology. Examples of sequencing technologies that can be used with the methods disclosed herein include, but are not limited to, the Illumina® sequencing-by-synthesis platform (Illumina, San Diego, Calif.), the SOLiD™ system (Applied Biosystems Corp.), pyrosequencing (e.g., 454 Life Sciences, subsidiary of Roche Diagnostics), sequencing techniques based on semiconductor detectors (e.g., the Ion Torrent® platform), nanopore sequencing (e.g., the Oxford Nanopore sequencing platform), DNA nanoball sequencing methods (e.g. Complete Genomics), sequencing by hybridization and any other suitable technology, or any technology that may be derived from any of the above technologies.

The disclosure provides methods that enable the mapping of the plurality of read-sets to the plurality of contigs. There are several publicly available computer programs for mapping reads to contig sequences. For example, sequencing reads can be used as queries to compare against datasets comprised of assembled or unassembled contig sequence, for example using a BLAST algorithm such as that described in any of the following references Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402; Zhang Z., Schwartz S., Wagner L., & Miller W. (2000), "A greedy algorithm for aligning DNA sequences", J Comput Biol 2000; 7(1-2):203-14; Zhang, J. & Madden, T. L. (1997) "PowerBLAST: A new network BLAST application for interactive or automated sequence analysis and annotation." Genome Res. 7:649-656.

Traditional paired-end sequencing data sets comprise pairs of reads sampled from the genome so as to indicate approximately the probability distribution of their separation on the genome. Barcode Tagged sequence read data sets yield "sets" or "bins" of sequence tagged reads, where each set is defined in practice by sharing a ligated barcode molecular tag sequence. The reads in each "set" sample a particular nucleic acid molecule (a subset of the genome or other target sequence sample) approximately uniformly. The subset of the genome being sampled may be a single segment corresponding to a single molecule of input DNA, or it may be multiple input segments.

The ordering and orientation problem relates to the challenge of determining the orientation and relative position of a pair of sequence contigs, both as adjacent segments of the genome, and among the four possible relative orientations.

Given a set of sequence reads sharing a common molecular tag and mapping to a common region of the target sequence or to two or more contigs in an obtained contig set (a common region of the genome, or a set of contigs known or believed to map to the same general vicinity, or even a set of contigs for which no mapping information is known), one may determine an order among the contigs as follows.

Provided that the nucleic acid molecules do not correspond directly to assembled contigs in content and in their endpoints, barcoded sequence sets derived from these nucleic acid molecules are in some embodiments used to assemble contig order and orientation as follows. Individual sequence reads on a sequence set are each individually mapped to a locus on a contig in the contig set corresponding to the target sequence of a sample. Commonly tagged sequences that derive from a single nucleic acid molecule are likely to map nearby to one another on a contig or contigs. If a commonly tagged set of sequence reads maps to more than one contig, in some embodiments the contigs are presumed to be near one another in the genomic sequence. In some embodiments, if a set of sequence reads maps to the ends of two contigs, the contigs are presumed to be adjacent and oriented such that the ends to which sequence reads map are adjacent to one another. In some embodiments, if a sequence read set spans three or more than three contigs, then the contig or contigs demonstrating complete coverage are placed in the interior of the contig order, and any one or two contigs demonstrating partial coverage, such as coverage biased toward an end of each contig, are positioned at an end or on opposite ends of the contig order. In some embodiments, middle contigs are unoriented. In some embodiments, if a sequence read set spans three or more than three contigs, then the contig or contigs demonstrating complete coverage are placed in the interior of the contig order and are unoriented, and any one or two contigs demonstrating partial coverage, such as coverage biased toward an end of each contig, are positioned at an end or on opposite ends of the contig order and are oriented such that the end of each contig demonstrating partial coverage is positioned adjacent to the internal contigs demonstrating full coverage.

In diploid genomes, it is often useful to know which allelic variants are physically linked on the same chromosome rather than mapping to the homologous position on a chromosome pair. Mapping an allele or other sequence to a specific physical chromosome of a diploid chromosome pair is known as the haplotype phasing. Short reads from high-throughput sequence data rarely allow one to directly observe which allelic variants are linked, particularly, as is most often the case, if the allelic variants are separated by a greater distance than the longest single read. Computational inference of haplotype phasing can be unreliable at long distances. Methods disclosed herein allow for determining which allelic variants are physically linked using allelic variants on read pairs.

In various cases, the methods and compositions of the disclosure enable the haplotype phasing of diploid or polyploid genomes with regard to a plurality of allelic variants. Methods described herein thus provide for the determination of linked allelic variants based on variant information from labeled sequence segments and/or assembled contigs using the same. Examples of allelic variants include, but are not limited to, those that are known from the 1000 genomes, UK10K, HapMap and other projects for discovering genetic variation among humans. Disease association to a specific gene can be revealed more easily by having haplotype phasing data as demonstrated, for example, by the finding of unlinked, inactivating mutations in both copies SH3TC2 leading to Charcot-Marie-Tooth neuropathy (Lupski J R, Reid J G, Gonzaga-Jauregui C, et al. *N. Engl. J. Med.* 362:1181-91, 2010) and unlinked, inactivating mutations in both copies of ABCG5 leading to hypercholesterolemia 9 (Rios J, Stein E, Shendure J, et al. *Hum. Mol. Genet.* 19:4313-18, 2010).

Humans are heterozygous at an average of 1 site in 1,000. In some cases, a single lane of data using high throughput sequencing methods can generate at least about 150,000,000 reads. Individual reads can be about 100 base pairs long. If one assumes input DNA fragments average 150 kbp in size and we get 100 paired-end reads per fragment, then one can expect to observe 30 heterozygous sites per set, i.e., per 100 read-pairs. Every read-pair containing a heterozygous site within a set is in phase (i.e., molecularly linked) with respect to all other read-pairs within the same set. This property enables greater power for phasing with sets as opposed to singular pairs of reads in some cases. With approximately 3 billion bases in the human genome, and one in one-thousand being heterozygous, there are approximately 3 million heterozygous sites in an average human genome. With about 45,000,000 read pairs that contain heterozygous sites, the average coverage of each heterozygous site to be phased using a single lane of a high throughput sequence method is about (15×), using a typical high throughput sequencing machine. A diploid human genome can therefore be reliably and completely phased with one lane of a high-throughput sequence data relating sequence variants from a sample that is prepared using the methods disclosed herein. In some examples, a lane of data can be a set of DNA sequence read data. In further examples, a lane of data can be a set of DNA sequence read data from a single run of a high throughput sequencing instrument.

As the human genome consists of two homologous sets of chromosomes, understanding the true genetic makeup of an individual requires delineation of the maternal and paternal copies or haplotypes of the genetic material. Obtaining a haplotype in an individual is useful in several ways. For example, haplotypes are useful clinically in predicting outcomes for donor-host matching in organ transplantation. Haplotypes are increasingly used to detect disease associations. In genes that show compound heterozygosity, haplotypes provide information as to whether two deleterious variants are located on the same allele (that is, 'in cis', to use genetics terminology) or on two different alleles ('in trans'), greatly affecting the prediction of whether inheritance of these variants is harmful, and impacting conclusions as to whether an individual carries a functional allele and a single nonfunctional allele having two deleterious variant positions, or whether that individual carries two nonfunctional alleles, each with a different defect. Haplotypes from groups of individuals have provided information on population structure of interest to both epidemiologists and anthropologists and informative of the evolutionary history of the human race. In addition, widespread allelic imbalances in gene expression have been reported, and suggest that genetic or epigenetic differences between allele phase may contribute to quantitative differences in expression. An understanding of haplotype structure will delineate the mechanisms of variants that contribute to allelic imbalances.

In certain embodiments, the methods disclosed herein comprise in vitro techniques to fix and capture associations among distant regions of a genome as needed for long-range linkage and phasing. In some cases, the method comprises constructing and sequencing one or more read-sets to deliver very genomically distant read pairs. Each read-set can comprise two or more reads that are labeled by a common barcode, which may represent two or more sequence segments from a common polynucleotide. In some cases, the interactions primarily arise from the random associations within a single polynucleotide. In some examples, the genomic distance between sequence segments can be inferred because sequence segments near to each other in a polynucleotide interact more often and with higher probability, while interactions between distant portions of the molecule are less frequent. Methods disclosed herein are used in some embodiments to label sequence segments that span the largest polynucleotide from an extraction.

The disclosure provides methods and compositions that can produce data to achieve extremely high phasing accuracy. In comparison to previous methods, the methods described herein can phase a higher proportion of the variants. Phasing can be achieved while maintaining high levels of accuracy. This phase information can be extended to longer ranges, for example greater than about 200 kbp, about 300 kbp, about 400 kbp, about 500 kbp, about 600 kbp, about 700 kbp, about 800 kbp, about 900 kbp, about 1 Mbp, about 2 Mbp, about 3 Mbp, about 4 Mbp, about 5 Mbp, about 10 Mbp, or longer than about 10 Mbp, up to an d including the entire length of a chromosome. In some embodiments, more than 90% of the heterozygous SNPs for a human sample can be phased at an accuracy greater than 99% using less than about 250 million reads, e.g. by using only 1 lane of Illumina HiSeq data. In other cases, more than about 40%, 50%, 60%, 70%, 80%, 90%, 95% or 99% of the heterozygous SNPs for a human sample can be phased at an accuracy greater than about 70%, 80%, 90%, 95%, or 99% using less than about 250 million or about 500 million reads, e.g. by using only 1 or 2 lanes of Illumina HiSeq data. For example, more than 95% or 99% of the heterozygous SNPs for a human sample can be phase at an accuracy greater than about 95% or 99% using less about 250 million or about 500 million reads. In further cases, additional variants can be captured by increasing the read length to about 200 bp, 250 bp, 300 bp, 350 bp, 400 bp, 450 bp, 500 bp, 600 bp, 800 bp, 1000 bp, 1500 bp, 2 kbp, 3 kbp, 4 kbp, 5 kbp, 10 kbp, 20 kbp, 50 kbp, or 100 kbp.

Methods and compositions disclosed herein allow for the investigation of meta-genomes, for example, those found in the human gut. Accordingly, the partial or whole genomic sequences of some or all organisms that inhabit a given ecological environment can be investigated. Examples include random sequencing of all gut microbes, the microbes found on certain areas of skin, and the microbes that live in toxic waste sites. The composition of the microbe population in these environments is determined using the compositions and methods described herein and as well as the aspects of interrelated biochemistries encoded by their respective genomes. Methods described herein enable meta-genomic studies from complex biological environments, for example, those that comprise more than 2, 3, 4, 5, 6, 7, 8, 9, 10, 12, 15, 20, 25, 30, 40, 50, 60, 70, 80, 90, 100, 125, 150, 175, 200, 250, 300, 400, 500, 600, 700, 800, 900, 1000, 5000, 10000 or more organisms and/or variants of organisms.

Accordingly, methods disclosed herein may be applied to intact human genomic DNA samples but may also be applied to a broad diversity of nucleic acid samples, such as reverse-transcribed RNA samples, circulating free DNA samples, cancer tissue samples, crime scene samples, archaeological samples, nonhuman genomic samples, or environmental samples such as environmental samples comprising genetic information from more than one organism, such as an organism that is not easily cultured under laboratory conditions.

High degrees of accuracy required by cancer genome sequencing can be achieved using the methods and systems described herein. Inaccurate reference genomes can make base-calling challenges when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in base-calling.

In some cases the individual suffers from or is suspected of suffering from a cancer for which genetic rearrangement is indicative of efficacious treatment regimen selection. The cancer may, for example, comprise a genetic rearrangement for which phase information is relevant to treatment selection, for example because of physical linkage information related to the disruption of multiple loci in the rearrangement.

In some cases the individual carries a combination of genetic alleles the activity of which is impacted by their phasing status. For example, an individual may carry an allele for which activity of a cis-acting transcription enhancer element is lost. The individual may also carry an allele encoding an active and an inactive version of the enzyme which the transcription enhancer regulates. If the variant enhancer and the inactive enzyme locus are in phase, then the individual is expected to have a chromosome harboring a defective enhancer element and a defective enzyme, and by consequence also harboring a functional enzyme having a healthy expression pattern. If instead the defective enhancer element and the defective enzyme are not in phase, then the individual may have a properly regulated defective enzyme, and an improperly regulated healthy enzyme, such that the individual lacks healthy expression of the healthy enzyme.

A sample is taken from the individual using any number of sample collection methods, such as collection methods consistent with the disclosure herein. In some cases the sample is collected so as to preserve intact chromatin complexes comprising native chromatin proteins and nucleic acids. In alternate cases nucleic acids are isolated from sample proteins, and chromatin or other nucleic acid binding polypeptides are subsequently added to reconstitute chromatin globs or other nucleic acid-protein globs.

Chromatin is cross-linked as disclosed herein or using other methods known to one in the art. Alternately, nucleic acid/polypeptide globs are reconstituted comprising bound complexes. In some cases these globs are cross-linked such that nucleic acid—polypeptide covalent bonds are formed. In some cases nucleic acid-polypeptide binding is sufficient to maintain glob integrity in the absence of cross-linking. Samples are collected and processed at a single site in some cases. Alternately, samples are collected at one site and transmitted to a second site for extraction, crosslinking or other downstream processing.

Nucleic acids bonds in at least one glob extracted from the sample are broken as disclosed herein, either through a specific or nonspecific endonuclease activity or using non-enzymatic reagents, such that double strand breaks internal to the molecule are generated. Double-stranded nucleic acid breaks are tagged by an oligonucleotide sequence such that the sequence adjacent to the break/tag junction can be obtained and mapped to the nucleic acid molecule or glob from which it was obtained.

In some embodiments, endonuclease treated globs are contacted to an array comprising barcoded oligo loci, each locus comprising a distinct population of oligos bound to the locus at their 3' end.

Tagged double-strand break and adjacent sequence is obtained, which in many embodiments represents predominantly internal break-adjacent sequence.

Sample processing and sequence determination occurs at a single site in some cases. Alternately, samples are processed at one site and transmitted to another site for extraction, crosslinking or other downstream processing.

Sequence adjacent to tagged double-strand breaks, comprising both internal sequence and sequence of oligo tags, is obtained and processed. Border-adjacent sequence is obtained and in some cases 'binned' such that sequence corresponding to a single glob end sequences is treated in common. End-adjacent sequence is mapped to a genomic sequence dataset comprising contigs and sequence reads. End adjacent sequence that uniquely maps to a single contig is used to group the contig or sequence read to which it maps in phase or physical linkage with other contigs or sequence reads to which similarly tagged or similarly binned end-adjacent reads map. In some cases account is taken of the fact that many end-adjacent reads will map to not one unique contig or sequence read but to sequence reads or contigs corresponding to two homologous chromosomes. In these cases, the presence of an end-adjacent read in the same bin or corresponding to the same nucleic acid glob is used in some cases to correctly map the contig or sequence read to a phase, physical linkage group or scaffold.

Sample sequence determination and mapping occurs at a single site in some cases. Alternately, sequences are determined at one site and transmitted to another site for mapping or other downstream processing.

Upon determination of phase information, the results are in some cases send directly to the individual from which the sample is taken. In alternate embodiments or in combination, the results are sent to a medical practitioner, counselor, pharmacist or related advisor. Results are sent in physical form in some cases, or alternately or in combination are sent in digital or electronic form.

In some cases results are used to inform a treatment selection, a treatment regimen selection, or a health or lifestyle choice for which genomic phase or physical linkage is relevant.

The systems and methods described herein may generate accurate long sequences from complex samples containing 2, 3, 4, 5, 6, 7, 8, 9, 10, 12, 15, 20 or more than 20 varying genomes. Mixed samples of normal, benign, and/or tumor origin may be analyzed, optionally without the need for a normal control. In some embodiments, samples comprising less than about 1000 ng, about 500 ng, about 200 ng, about 100 ng, about 50 ng, about 20 ng, about 10 ng, or even as little as hundreds of genome equivalents, can be utilized to generate accurate long sequences. Systems and methods described herein may allow for detection of large scale structural variants and rearrangements, Phased variant calls may be obtained over long sequences spanning about 1 kbp, about 2 kbp, about 5 kbp, about 10 kbp, 20 kbp, about 50 kbp, about 100 kbp, about 200 kbp, about 500 kbp, about 1 Mbp, about 2 Mbp, about 5 Mbp, about 10 Mbp, about 20 Mbp, about 50 Mbp, or about 100 Mbp or more nucleotides. For example, a phase variant call may be obtained over long sequences spanning about 1 Mbp or about 2 Mbp.

Haplotypes determined using the methods and systems described herein may be assigned to computational resources, for example, computational resources over a network, such as a cloud system. Similarly, contig information can be obtained using computational resources such as cloud system resources. Short variant calls can be corrected, if necessary, using relevant information that is stored in the computational resources. Structural variants can be detected based on the combined information from short variant calls and the information stored in the computational resources. Problematic parts of a genome, such as segmental duplications, regions prone to structural variation, the highly variable and medically relevant MHC region, centromeric and telomeric regions, and other heterochromatic regions including but limited to those with repeat regions, low sequence accuracy, high variant rates, ALU repeats, segmental duplications, or any other relevant problematic parts known in the art, can be assembled or reassembled for increased accuracy.

A sample type can be assigned to the sequence information either locally or in a networked computational resource, such as a cloud. In cases where the source of the information is known, for example, when the source of the information is from a cancer or normal tissue, the source can be assigned to the sample as part of a sample type. Other sample type examples generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence can be determined and optionally output.

The methods of the present disclosure can be used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present disclosure can be used to amplify target nucleic acid for DNA hybridization studies to determine the presence or absence of polymorphisms. The polymorphisms, or alleles, can be associated with diseases or conditions such as genetic disease. In other cases the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

Methods and compositions of the disclosure can be used for diagnostic, prognostic, therapeutic, patient stratification, drug development, treatment selection, and screening purposes. The present disclosure provides the advantage that many different target molecules can be analyzed at one time from a single biomolecular sample using the methods of the disclosure. This allows, for example, for several diagnostic tests to be performed on one sample.

Methods and compositions of the present disclosure can be used in genomics. Methods described herein can provide an answer rapidly, which is very desirable for this type of technology. The methods and composition described herein can be used in the process of finding biomarkers that may be used for diagnostics and/or prognostics, and/or as indicators of health, disease, or as part of a pharmaceutical selection regime. The methods and compositions described herein can be used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously, which will provide the most information regarding the particular screening being performed.

The methods and compositions of the disclosure can be used in gene expression analysis. The methods described herein can be used to discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. The process of the present disclosure is able to detect infectious diseases, genetic diseases, and cancer. It is also useful in environmental monitoring, forensics, and food science. Examples of genetic analyses that can be performed on nucleic acids include e.g., SNP detection, STR detection, RNA expression analysis, promoter methylation, gene expression, virus detection, viral subtyping and drug resistance.

The present methods can be applied to the analysis of biomolecular samples obtained or derived from a subject so as to determine whether a diseased cell type is present in the sample, the stage of the disease, the prognosis for the subject, the ability to the subject to respond to a particular treatment, or the best treatment for the subject. The present methods can also be applied to identify biomarkers for a particular disease.

The methods described herein can be used in the diagnosis of a condition. As used herein, the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. For example, a blood sample can be assayed according to any of the methods described herein to determine the presence and/or quantity of markers of a disease or malignant cell type in the sample, thereby diagnosing or staging the a disease or a cancer. The methods and composition described herein can also be used for the diagnosis and/or prognosis of a condition.

Numerous immunologic, proliferative and malignant diseases and disorders can be amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis *nodosa*, and inflammatory bowel disease, allograft rejection and tissue destructive from allergic reactions to infectious microorganisms or to environmental antigens.

Proliferative diseases and disorders that may be evaluated by the methods of the disclosure include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the disclosure include both hematologic malignancies and solid tumors. Hematologic malignancies can be amenable to the methods of the disclosure, especially when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple my eloma, myelodysplastic disorders, myeloproliferative disorders, myelofibroses, atypical immune lymphoproliferations and plasma cell disorders. Plasma cell disorders that may be evaluated by the methods of the disclosure include multiple myeloma, amyloidosis and Waldenstrom's macroglobulinemia. Examples of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present disclosure. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

The methods described herein can be used to diagnose pathogen infections (e.g. infections by intracellular bacteria and viruses) by determining the presence and/or quantity of markers of bacterium or virus, respectively, in the sample.

A wide variety of infectious diseases can be detected by the process of the present disclosure. The infectious diseases can be caused by bacterial, viral, parasite, and fungal infectious agents. The resistance of various infectious agents to drugs can also be determined using the present disclosure.

Bacterial infectious agents which can be detected by the present disclosure include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., Corynebacteria, *Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present disclosure include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present disclosure include human immunodeficiency virus, human T-cell lymphocytotrophic virus, hepatitis viruses (e.g., Hepatitis B Virus and Hepatitis C Virus), Epstein-Barr virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present disclosure include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

The present disclosure can also be useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present disclosure. Thus, the target molecules detected using the compositions and methods of the disclosure can be either patient markers (such as a cancer marker) or markers of infection with a foreign agent, such as bacterial or viral markers.

The methods and compositions of the present disclosure can be used to identify and/or quantify a target molecule whose abundance is indicative of a biological state or disease condition, for example, blood markers that are upregulated or downregulated as a result of a disease state.

In some embodiments, the methods and compositions of the present disclosure can be used for detecting cytokine expression. The sensitivity of the methods described herein can be helpful for early detection of cytokines, e.g., as biomarkers of a condition, diagnosis or prognosis of a disease such as cancer, and the identification of subclinical conditions.

In some embodiments, the present disclosure provides methods for associating a first sequence segment and a second sequence segment. In some cases, the methods comprise: (a) crosslinking a DNA library comprising a first DNA molecule, wherein the first DNA molecule comprises the first sequence segment and the second sequence segment; (b) isolating the first sequence segment and the second sequence segment in a first reaction volume; and (c) attaching a first label to the first sequence segment and a second label to the second sequence segment. In some cases, the methods comprise: (a) crosslinking a DNA library comprising a first DNA molecule, wherein the first DNA molecule comprises the first sequence segment and the second sequence segment; (b) isolating the first sequence segment and the second sequence segment in a first reaction volume; (c) releasing the first sequence segment and the second sequence segment from the crosslinking; and (d) linking the first sequence segment and the second sequence segment.

The method can further comprise severing the first DNA molecule. The first DNA molecule can be severed by any known method in the art, including but not limited to the chemical, enzymatic, and mechanical fragmentation methods disclosed in the present application. For example, the first DNA molecule can be severed using a restriction enzyme. Alternatively, the first DNA molecule can be severed by ultraviolet irradiation. The first DNA molecule can be severed into the first sequence segment and the second sequence segment, which may have blunt-ends or overhangs. In some cases, the overhangs can be filled in by modified nucleotides, such as sulfated or biotinylated nucleotides. In some cases, adaptor oligonucleotides can be hybridized and/or ligated to the blunt-ends or overhangs. The adaptor oligonucleotides can be any known adaptor in the art, including but not limited to those disclosed in the present application.

The first sequence segment and the second sequence segment can be bound to a plurality of association molecules. In some cases, the association molecules can comprise amino acids. For example, the association molecules can comprise peptides or proteins (e.g. histones, packing proteins such as H1 and protamine, nucleic acid binding proteins such as transcription factors, inactivated DNA repair proteins, double-stranded DNA binding proteins, inactivated topoisomerase such as bacterial topoisomerase or topoisomerase I or II class enzymes, transposase, or other polypeptide that binds DNA).

In some cases, the association molecule comprises amino acids. In some cases, the association molecule comprises peptides or proteins (e.g. histones, for example comprising at least one of H2A, H2B, H3A, H3B, H4A and H4B, a transcription factor, a double-stranded DNA binding protein such as a topoisomerase (bacterial, type I or type II), a restriction endonuclease, a transposase, a transcription factor or packing proteins such as H1 and protamine). In some cases the binding protein is modified by chemical treatment or targeted mutagenesis to lack enzymatic activity. In some cases the binding protein is modified by chemical treatment or targeted mutagenesis to lack enzymatic activity but retain nucleic acid binding. In some cases the association molecule comprises a nonpolypeptide such as protamine, spermine, spermidine or other positively charged molecule. In some cases, the association molecules comprise nanoparticles. The nanoparticles can be magnetic, which may facilitate the isolation of the cross-linked sequence segments. The nanoparticles comprise silicon in some cases, and in some cases are coated with a positively charged substance, a substance to facilitate cross-linking to a nucleic acid, or a substance that is both positively charged and capable of facilitating cross-linking to a nucleic acid.

Further, the association molecules can be from a different source than the first DNA molecule. In some examples, the first DNA molecule can be from a first human subject, whereas the association molecules can be from a second human subject. In other examples, the first DNA molecule can be from a mammal (e.g. human), whereas the association molecules can be from another eukaryotic organism. In further examples, the first DNA molecule can be from a plant cell or a prokaryote, whereas the association molecules can be from a eukaryotic organism.

In some cases, the association molecules can comprise nanoparticles. The nanoparticles can be magnetic, which may facilitate the isolation of the cross-linked sequence segments. Further, the association molecules can be from a different source than the first DNA molecule. In some examples, the first DNA molecule can be from a first human subject, whereas the association molecules can be from a second human subject. In other examples, the first DNA molecule can be from a mammal (e.g. human), whereas the association molecules can be from another eukaryotic organism. In further examples, the first DNA molecule can be from a plant cell or a prokaryote, whereas the association molecules can be from a eukaryotic organism.

In some embodiments the first reaction volume is an aqueous droplet. The first sequence segment and the second sequence segment can be isolated in the first reaction volume using various techniques, including but not limited to emulsions, microfluidic devices, and liposomes, lipid bilayers and micelles.

The use of microfluidics allow for more precise control of the composition within the reaction volume, yielding greater control of the number of aggregates, reagents and enzymes in each reaction volume. The linear nature of microfluidic channels can allow for optical scanning of the reaction volume for various measurements related to the efficiency of reactions or the presence or absence of particular components. In some cases, junctions within the microfluidic channel can be used to divert and/or discard compartments that do not meet certain criteria, based on optical scanning or other sensing. Alternatively, the aqueous droplet can also be generated as a liposome or a micelle surrounded by relative thin lipid mono-(micelle) or bi-(liposome) layers. In some examples, the amphipathic layer(s) can comprise phospholipids. However, nearly any amphipathic molecule may be used to form such compartments. Using liposomes/micelles may allow for substantially simpler and more feasible passing of reagents across the membrane, thus allowing for more flexibility in the reaction environment. In some cases, the lipid layer(s) can comprise phospholipids. In some cases, anionic phospholipids may be used to coat, rather than fully encapsulate, the cross-linked sequence segments to provide a more confined reaction environment at the expense of space for enzymes and reagents.

The first reaction volume can comprise a single DNA molecule and not any other DNA molecule. The DNA library can comprise a plurality of DNA molecules that are isolated in a plurality of reaction volumes. Further, the DNA molecules can be isolated in the reaction volumes under conditions such that a substantial percentage of the reaction volumes comprise a single DNA molecule or no DNA molecules at all. For example, more than about 50%, about 60%, about 70%, about 75%, about 80%, about 85%, about 90%, about 91%, about 92%, about 93%, about 94%, about 95%, about 96%, about 97%, about 98%, about 99%, about 99.9%, about 99.99%, about 99.999%, or about 99.9999% of the reaction volumes can comprise 0 or 1 DNA molecules.

In some cases, a first oligo label and a second oligo label are identical. In other cases, the first label and the second label are different. The first label and the second label can be polynucleotides. Further, the first label and the second label can each comprise one or more elements selected from the group consisting of a primer, a barcode and a restriction site. In some examples, the first label and the second label each comprise a barcode. The labels can also comprise specific sequences indicating the location of the barcode. The first label and the second label can be produced from a template in the first reaction volume. In some cases, the first label and the second label can be produced by amplification of a linear template (e.g. PCR). In other cases, the first label and the second label can be produced by Rolling Circle Amplification (RCA) of a circular template. The RCA product may be further digested to yield a plurality of labels. In some cases, the labels can also be digested or modified (e.g. adenylated), such as to generate complementary overhangs for attachment to the sequence segments. The labels can be attached to the sequence segments by ligation or by hybridization and extension with a DNA polymerase. The labels can be attached directly to the sequence segments, or indirectly to adaptor oligonucleotides that are ligated or hybridized to the sequence segments.

The first sequence segment and the second sequence segment can be released from the crosslinking using heat or chemical agents. In some cases, the crosslinks can be reversed. In some cases, the first sequence segment and the second sequence segment are further digested to generate new ends (e.g. with a different restriction enzyme). The first sequence segment and the second sequence segment can be hybridized and/or linked by a ligase. The sequence segments within a single reaction volume may link to one another and generate many hybrid molecules. In some cases, the linked sequence segments may be previously distant on the original DNA molecule.

Sequencing adaptors can be further linked to the first sequence segment and/or the second sequence segment. The sequence information of the first sequence segment and/or the second sequence segment can be obtained by a sequencing method. The sequencing method can be any known sequencing method in the art, including but not limited to the sequencing technologies disclosed in the present application. For example, the sequencing method can be a microarray analysis (e.g. comparative hybridization) or a high-throughput sequencing technique. Using the sequence information, the first sequence segment and the second sequence segment can be associated to one another. For example, the first sequence segment and the second sequence segment can comprise a same barcode and be binned into a read-set. The first sequence segment and the second sequence segment can be associated based on the first label and the second label. In some cases, the sequence information is also used to assemble a plurality of contigs. In certain cases, the sequence information is used to assemble the first DNA molecule. In further cases, the sequence information is used to assemble a genome. The genome can be assembled by aligning reads to a reference genome, or by de novo assembly.

The labeled or linked sequence segments can be analyzed and/or characterized. In some cases, the labeled or linked sequence segments can be isolated (e.g. by phase separation), filtered and/or washed to retain only the sequence segments of interest. In some cases, the size of the DNA molecules in the DNA library may be estimated (e.g. by gel electrophoresis or pulsed field gel electrophoresis (PFGE)) and used to calculate an expected range (in base pairs) of the sequence segments.

In some aspects, the present disclosure provides a composition comprising at least one aqueous droplet. The aqueous droplet comprises in some cases: a nucleic acid comprising a first sequence segment and a second sequence segment. In some embodiments the nucleic acid is not bound by any additional molecule, while in other embodiments the nucleic acid is bound by a nucleic acid binding molecule configured so as to bind the first sequence segment and the second sequence segment. In many embodiments the additional molecule is covalently bound to the nucleic acid molecule, for example by formaldehyde or psoralin.

The aqueous droplet comprises a polymerase in some embodiments. In certain cases, the aqueous droplet further comprises a primer. In particular cases, the aqueous droplet comprises a restriction enzyme. In various cases, the aqueous droplet comprises a ligase. Examples of polymerases, primers, restriction enzymes and ligases are known in the art, including but not limited to those provided in the present disclosure.

In some cases, the aqueous droplet can be surrounded by an oil or an organic phase. In further cases, the aqueous droplet can be within a microfluidic device. The aqueous droplet in many embodiments is surrounded by an immiscible layer to form a micelle or an immiscible bilayer to form a liposome.

The aqueous droplet comprises a plurality of molecular tagged or barcoded oligonucleotides in some cases. In many cases these molecularly tagged or barcoded oligonucleotide molecules have identical sequences. In further embodiments the molecularly tagged or barcoded oligonucleotide molecules have identical molecular tag or barcode sequences. In other cases the aqueous droplet comprises molecular tagged or barcoded oligonucleotides that sort into at least two populations, each population characterized by a distinct molecular tag or barcode sequence.

The polynucleotides used in the methods disclosed herein can be derived from multiple samples from the same individual, samples from different individuals, or combinations thereof. In some cases, a sample can comprise a plurality of polynucleotides from a single individual. In some cases, a sample can comprise a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., or a mammal, such as a human. Samples can also be artificially derived, such as by chemical synthesis. In some embodiments, the samples can comprise DNA. In some embodiments, the samples can comprise genomic DNA. In some embodiments, the samples can comprise mitochondrial DNA, chloroplast DNA, plasmid DNA, bacterial artificial chromosomes, yeast artificial chromosomes, oligonucleotide tags, or combinations thereof. In some embodiments, the samples can comprise DNA generated by primer extension reactions using any suitable combination of primers and a DNA polymerase, including but not limited to polymerase chain reaction (PCR), reverse transcription, and combinations thereof. In cases wherein the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

In some embodiments, nucleic acid template molecules (e.g., DNA or RNA) are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present disclosure include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the disclosure. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the disclosure, such as to remove excess or unwanted reagents, reactants, or products.

Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). In some cases, the nucleic acids can be first extract from the biological samples and then cross-linked in vitro. In some cases, native association proteins (e.g. histones) can be further removed from the nucleic acids.

In some cases, the methods disclosed herein can be applied to any high molecular weight double stranded DNA molecule including, for example, DNA isolated from tissues, cell culture, bodily fluids, animal tissue, plant, bacteria, fungi, viruses, etc.

In some cases, each of the plurality of independent samples can independently comprise at least about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid material. In some embodiments, each of the plurality of independent samples can independently comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid.

As used herein, the term "adapter oligonucleotide" refers to any oligonucleotide having a sequence, at least a portion of which is known, that can be joined to a target polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide.

Adapters of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." In some embodiments, end repair is performed to generate blunt end 5' phosphorylated nucleic acid ends using commercial kits, such as those available from Epicentre Biotechnologies (Madison, Wis.).

Different adapters can be joined to target polynucleotides in sequential reactions or simultaneously. For example, the first and second adapters can be added to the same reaction. Adapters can be manipulated prior to combining with target polynucleotides. For example, terminal phosphates can be added or removed.

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop").

In some cases, the first adapter oligonucleotides in a plurality of first adapter oligonucleotides having different barcode sequences can comprise a sequence element common among all first adapter oligonucleotides. In some embodiments, all second adapter oligonucleotides can comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification).

In some embodiments, an adapter oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. For example, the complementary overhangs can be about 1, 2, 3, 4, 5 or 6 nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length. In some examples, the adaptors can be about 10 to about 50 nucleotides in length. In further examples, the adaptors can be about 20 to about 40 nucleotides in length.

As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes can be at least 3, 4, 5, 6, 7, 8, 9, 10, 11, 12, 13, 14, 15, or more nucleotides in length. For example, barcodes can be at least 10, 11, 12, 13, 14, or 15 nucleotides in length. In some embodiments, barcodes can be shorter than 10, 9, 8, 7, 6, 5, or 4 nucleotides in length. For example, barcodes can be shorter than 10 nucleotides in length. In some embodiments, barcodes associated with some polynucleotides are of different length than barcodes associated with other polynucleotides.

In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some examples, 1, 2 or 3 nucleotides can be mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some examples, each barcode can differ from every other barcode by in at least 2, 3, 4 or 5 positions.

In some embodiments, both a first site and a second site comprise at least one of a plurality of barcode sequences. In some embodiments, barcodes for second sites are selected independently from barcodes for first adapter oligonucleotides. In some embodiments, first sites and second sites having barcodes are paired, such that sequences of the pair comprise the same or different one or more barcodes. In some embodiments, the methods of the disclosure further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

In eukaryotes, genomic DNA is packed into chromatin to consist as chromosomes within the nucleus. The basic structural unit of chromatin is the nucleosome, which consists of 146 base pairs (bp) of DNA wrapped around a histone octamer. The histone octamer consists of two copies each of the core histone H2A-H2B dimers and H3-H4 dimers. Nucleosomes are regularly spaced along the DNA in what is commonly referred to as "beads on a string".

The assembly of core histones and DNA into nucleosomes is mediated by chaperone proteins and associated assembly factors. Nearly all of these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

In general, two in vitro methods have been developed for reconstituting or assembling chromatin. One method is ATP-independent, while the second is ATP-dependent. The ATP-independent method for reconstituting chromatin involves the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

As used herein, the terms "fragment", "segment", or "sequence segment" can refer to a piece of polynucleotide derived or prepared from an original, larger nucleic acid molecule. Unless otherwise specified, the terms are used interchangeably herein.

The methods disclosed herein can be applied to any type of fragmented double stranded polynucleotide including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.).

Polynucleotides obtained from biological samples can be fragmented to produce suitable fragments or segments for analysis. Polynucleotides may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In some embodiments, nucleic acid from a biological sample is fragmented by sonication. In other embodiments, nucleic acid is fragmented by a hydroshear instrument. Generally, individual nucleic acid molecules can be from about 2 kb to about 40 kb. In some cases, the nucleic acids can be from about 6 kb to about 10 kb. Nucleic acid molecules may be single-stranded, double-stranded, or double-stranded with single-stranded regions (for example, stem- and loop-structures).

In some cases, cross-linked polynucleotides may be subjected to a size selection step. Size selection of the nucleic acids may be performed to cross-linked polynucleotides below or above a certain size. Size selection may further be affected by the frequency of cross-links and/or by the fragmentation method, for example by choosing a frequent or rare cutter restriction enzyme. In some embodiments, a composition may be prepared comprising cross-linking a DNA molecule in the range of about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

Sample polynucleotides can be fragmented into a population of fragmented polynucleotides of one or more specific size range(s). In some cases, fragments can be generated from at least about 1, about 2, about 5, about 10, about 20, about 50, about 100, about 200, about 500, about 1000, about 2000, about 5000, about 10,000, about 20,000, about 50,000, about 100,000, about 200,000, about 500,000, about 1,000,000, about 2,000,000, about 5,000,000, about 10,000,000, or more genome-equivalents of starting DNA. Fragmentation may be accomplished by methods known in the art, including chemical, enzymatic, and mechanical fragmentation.

In some cases, the fragments can have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600,000, about 700,000, about 800,000, about 900,000, about 1,000,000, about 2,000,000, about 5,000,000, about 10,000,000, or more nucleotides. In some examples, the fragments can have an average length from about 1 kb to about 10 Mb. In other examples, the fragments can have an average length from about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb).

In some cases, the fragments can have an average length less than about 10 Mb, less than about 5 Mb, less than about 1 Mb, less than about 500 kb, less than about 200 kb, less than about 100 kb, or less than about 50 kb. In other cases, the fragments have an average length more than about 5 kb, more than about 10 kb, more than about 50 kb, more than about 100 kb, more than about 200 kb, more than about 500 kb, more than about 1 Mb, more than about 5 Mb, or more than about 10 Mb.

The fragmentation can be accomplished mechanically, comprising subjection nucleic acid molecules to acoustic sonication. In some cases, the fragmentation can comprise treating the polynucleotide with one or more enzymes under conditions suitable for the one or more enzymes to generate double-stranded nucleic acid breaks. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$.

In some cases, the fragmentation can comprise treating the sample DNA molecules with one or more endonucleases. A number of endonuclecase enzymes are contemplated herein, such as restriction endonucleases but also enzymes having nonspecific endonuclease activity such as some DNA repair enzymes, topoisomerases, transposases, and some DNA recombination mediating enzymes.

Fragmentation can produce fragments having 5' overhangs, 3' overhangs, blunt ends, or a combination thereof. In some embodiments, the polynucleotide can be cleaved to generate one or more overhangs with predictable sequence(s). In some embodiments, the method includes the step of size selecting the fragments via standard methods such as column purification or isolation from an agarose gel.

In some cases, the 5' and/or 3' end nucleotide sequences of fragmented polynucleotides are not modified prior to ligation. In some examples, fragmentation by a restriction endonuclease can be used to leave a predictable overhang, followed by ligation with a nucleic acid end comprising an overhang complementary to the predictable overhang on a polynucleotide fragment. In other examples, cleavage by an enzyme that leaves a predictable blunt end can be followed by ligation of blunt-ended polynucleotide fragments to nucleic acids, such as adapters, oligonucleotides, or polynucleotides, comprising a blunt end. In some embodiments, the fragmented polynucleotide can be blunt-end polished (or "end repaired") to produce DNA fragments having blunt ends, prior to being joined to adapters. The blunt-end polishing step may be accomplished by incubation with a suitable enzyme, such as a DNA polymerase that has both 3' to 5' exonuclease activity and 5' to 3' polymerase activity, for example T4 polymerase. In some embodiments, end repair can be followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. For example, the end repair can be followed by an addition of 1, 2, 3, 4, 5, or 6 nucleotides.

Polynucleotide fragments having an overhang can be joined to one or more nucleic acids, such as oligonucleotides, adapter oligonucleotides, or polynucleotides, having a complementary overhang, such as in a ligation reaction. For example, a single adenine can be added to the 3' ends of end repaired DNA fragments using a template independent polymerase, followed by ligation to one or more adapters each having a thymine at a 3' end. In some cases, nucleic acids, such as oligonucleotides or polynucleotides can be joined to blunt end double-stranded DNA molecules which have been modified by extension of the 3' end with one or more nucleotides followed by 5' phosphorylation. In some cases, extension of the 3' end may be performed with a polymerase such as, Klenow polymerase or any of the suitable polymerases provided herein, or by use of a terminal deoxynucleotide transferase, in the presence of one or more dNTPs in a suitable buffer that can contain magnesium.

Polynucleotides fragments having blunt ends can be joined to one or more adapters comprising a blunt end. Phosphorylation of 5' ends of DNA fragment molecules may be performed for example with T4 polynucleotide kinase in a suitable buffer containing ATP and magnesium. The fragmented DNA molecules may optionally be treated to dephosphorylate 5' ends or 3' ends, for example, by using enzymes known in the art, such as phosphatases.

As used herein, with respect to two polynucleotides such as an adapter oligonucleotide and a target polynucleotide, the terms "connecting", "joining" or "ligating" can refer to the covalent attachment of two separate nucleic acid segments to produce a single larger polynucleotide with a contiguous backbone. Methods for joining two nucleic acid segments are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, each of which is herein incorporated by reference in its entirety. In some embodiments, an adapter oligonucleotide is joined to a target polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

Ligation can be between nucleic acid segments having hybridizable sequences, such as complementary overhangs. Ligation can also be between two blunt ends. Generally, a 5' phosphate is utilized in a ligation reaction. The 5' phosphate can be provided by the target polynucleotide, the adapter oligonucleotide, or both. 5' phosphates can be added to or removed from sequence segments to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some cases, both of the two ends joined in a ligation reaction (e.g. an adapter end and a target polynucleotide end) provide a 5' phosphate, such that two covalent linkages are made in joining the two ends. In other cases, only one of the two ends joined in a ligation reaction (e.g. only one of an adapter end and a target polynucleotide end) provides a 5' phosphate, such that only one covalent linkage is made in joining the two ends.

In some cases, only one strand at one or both ends of a target polynucleotide is joined to an adapter oligonucleotide. In other cases, both strands at one or both ends of a target polynucleotide are joined to an adapter oligonucleotide. In some cases, 3' phosphates are removed prior to ligation. In some cases, an adapter oligonucleotide is added to both ends of a target polynucleotide, wherein one or both strands at each end are joined to one or more adapter oligonucleotides. When both strands at both ends are joined to an adapter oligonucleotide, joining can be followed by a cleavage reaction that leaves a 5' overhang that can serve as a template for the extension of the corresponding 3' end, which 3' end may or may not include one or more nucleotides derived from the adapter oligonucleotide. A target polynucleotide can be joined to a first adapter oligonucleotide on one end and a second adapter oligonucleotide on the other end. Alternatively, two ends of a target polynucleotide are joined to the opposite ends of a single adapter oligonucleotide. In some cases, the target polynucleotide and the adapter oligonucleotide to which it is joined comprise blunt ends. Separate ligation reactions can be carried out for each sample, using a different first adapter oligonucleotide comprising at least one barcode sequence for each sample, such that no barcode sequence is joined to the target polynucleotides of more than one sample. A sequence segment or a polynucleotide that has an adapter oligonucleotide joined to it is considered "tagged" by the joined adapter.

In some cases, the ligation reaction can be performed at a sequence segment or polynucleotide concentration of about less than about 0.1 ng/uL, about 0.2 ng/uL, about 0.3 ng/uL, about 0.4 ng/uL, about 0.5 ng/uL, about 0.6 ng/uL, about 0.7 ng/uL, about 0.8 ng/uL, about 0.9 ng/uL, about 1.0 ng/uL, about 1.2 ng/uL, about 1.4 ng/uL, about 1.6 ng/uL, about 1.8 ng/uL, about 2.0 ng/uL, about 2.5 ng/uL, about 3.0 ng/uL, about 3.5 ng/uL, about 4.0 ng/uL, about 4.5 ng/uL, about 5.0 ng/uL, about 6.0 ng/uL, about 7.0 ng/uL, about 8.0 ng/uL, about 9.0 ng/uL, about 10 ng/uL, about 15 ng/uL, about 20 ng/uL, about 30 ng/uL, about 40 ng/uL, about 50 ng/uL, about 60 ng/uL, about 70 ng/uL, about 80 ng/uL, about 90 ng/uL, about 100 ng/uL, about 150 ng/uL, about 200 ng/uL, about 300 ng/uL, about 400 ng/uL, about 500 ng/uL, about 600 ng/uL, about 800 ng/uL, or about 1000 ng/uL. In some cases, the ligation reaction can be performed at a sequence segment or polynucleotide concentration of about greater than about 0.1 ng/uL, about 0.2 ng/uL, about 0.3 ng/uL, about 0.4 ng/uL, about 0.5 ng/uL, about 0.6 ng/uL, about 0.7 ng/uL, about 0.8 ng/uL, about 0.9 ng/uL, about 1.0 ng/uL, about 1.2 ng/uL, about 1.4 ng/uL, about 1.6 ng/uL, about 1.8 ng/uL, about 2.0 ng/uL, about 2.5 ng/uL, about 3.0 ng/uL, about 3.5 ng/uL, about 4.0 ng/uL, about 4.5 ng/uL, about 5.0 ng/uL, about 6.0 ng/uL, about 7.0 ng/uL, about 8.0 ng/uL, about 9.0 ng/uL, about 10 ng/uL, about 15 ng/uL, about 20 ng/uL, about 30 ng/uL, about 40 ng/uL, about 50 ng/uL, about 60 ng/uL, about 70 ng/uL, about 80 ng/uL, about 90 ng/uL, about 100 ng/uL, about 150 ng/uL, about 200 ng/uL, about 300 ng/uL, about 400 ng/uL, about 500 ng/uL, about 600 ng/uL, about 800 ng/uL, or about 1000 ng/uL. For example, the ligation can be performed at a sequence segment or polynucleotide concentration of about 100 ng/uL, about 150 ng/uL, about 200 ng/uL, about 300 ng/uL, about 400 ng/uL, or about 500 ng/uL. In some cases, the ligation reaction can be performed at a sequence segment or polynucleotide concentration of about 0.1 to 1000 ng/uL, about 1 to 1000 ng/uL, about 1 to 800 ng/uL, about 10 to 800 ng/uL, about 10 to 600 ng/uL, about 100 to 600 ng/uL, or about 100 to 500 ng/uL.

In some cases, the ligation reaction can be performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In some cases, the ligation reaction can be performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. For example, the ligation reaction can be performed for about 30 minutes to about 90 minutes. In some examples, joining of an adapter to a polynucleotide produces a joined polynucleotide having a 3' overhang comprising a nucleotide sequence derived from the adapter.

In some cases, after joining at least one adapter oligonucleotide to a polynucleotide, the 3' end of one or more polynucleotides is extended using the one or more joined adapter oligonucleotides as template. For example, an adapter comprising two hybridized oligonucleotides that is joined to only the 5' end of a polynucleotide allows for the extension of the unjoined 3' end of the polynucleotide using the joined strand of the adapter as template, concurrently with or following displacement of the unjoined strand. Both strands of an adapter comprising two hybridized oligonucleotides may be joined to a polynucleotide such that the joined product has a 5' overhang, and the complementary 3' end can be extended using the 5' overhang as template. In some further examples, a hairpin adapter oligonucleotide can be joined to the 5' end of a polynucleotide. In some cases, the 3' end of the polynucleotide that is extended comprises one or more nucleotides from an adapter oligonucleotide. For target polynucleotides to which adapters are joined on both ends, extension can be carried out for both 3' ends of a double-stranded polynucleotide having 5' overhangs. This 3' end extension, or "fill-in" reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5' overhangs that are filled in by extension of the complementary strands' 3' ends, the product is completely double-stranded. Extension can be carried out by any suitable polymerase known in the art, such as a DNA polymerase, many of which are commercially available. DNA polymerases can comprise DNA-dependent DNA polymerase activity, RNA-dependent DNA polymerase activity, or DNA-dependent and RNA-dependent DNA polymerase activity. DNA polymerases can be thermostable or non-thermostable. Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof 3' end extension can be performed before or after pooling of polynucleotides from independent samples.

The disclosure further provides methods for the enrichment and/or analysis of nucleic acids. The enrichment method can be a solution-based format. The nucleic acid can be labeled with a labeling agent. The nucleic acid can be cross-linked to one or more association molecules that are labeled with a labeling agent. Examples of labeling agents include but are not limited to biotin, polyhistidine tags, and chemical tags (e.g. alkyne and azide derivatives used in Click Chemistry methods). Further, the labeled target nucleic acid can be captured and thereby enriched by using a capturing agent. The capturing agent can be streptavidin and/or avidin, an antibody, a chemical moiety (e.g. alkyne, azide), or any biological, chemical, physical, or enzymatic agents used for affinity purification known in the art.

In some cases, immobilized or non-immobilized nucleic acid probes can be used to capture the nucleic acids. For example, the polynucleotides can be enriched from a sample by hybridization to the probes on a solid support or in solution. In some examples, the sample can be a genomic sample. In some examples, the probes can be an amplicon. The amplicon can comprise a predetermined sequence. Further, the hybridized nucleic acids can be washed and/or eluted off of the probes. The nucleic acid can be a DNA, RNA, cDNA, or mRNA molecule.

In some cases, the enrichment method can comprise contacting the sample comprising the nucleic acid to the probes and binding the nucleic acid to a solid support. In some cases, the sample can be fragmented using chemical, physical or enzymatic methods to yield the nucleic acids. In some cases, the probes can be specifically hybridized to the nucleic acids. In some cases, the nucleic acids can have an average size of about 50 to 5000, about 50 to 2000, about 100 to 2000, about 100 to 1000, about 200 to 1000, about 200 to 800, or about 300 to 800, about 300 to 600, or about 400 to 600 nucleotide residues. The nucleic acids can be further separated from the unbound nucleic acids in the sample. The solid support can be washed and/or eluted to provide the enriched nucleic acids. In some examples, the enrichment steps can be repeated for about 1, 2, 3, 4, 5, 6, 7, 8, 9, or 10 times. For example, the enrichment steps can be repeated for about 1, 2, or 3 times.

Figure 4:
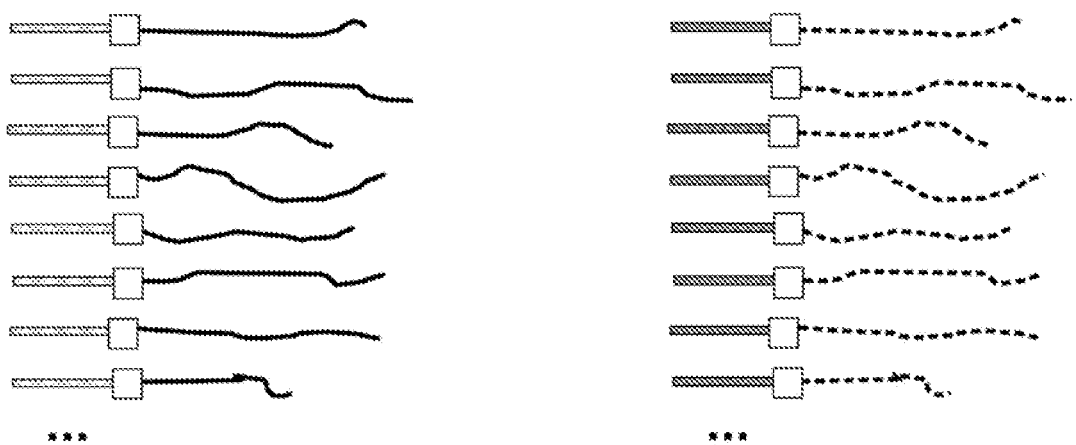
FIG. 4 diagrams that after the digested glob DNA is attached to the barcoded oligonucleotides corresponding to its sector, the result is a collection of DNA molecules that have oligonucleotides, junction, and glob DNA fragments.

In some cases, the enrichment method can comprise providing probe derived amplicons wherein the probes for amplification are attached to a solid support. The solid support can comprise support-immobilized nucleic acid probes to capture specific polynucleotides from a sample. The probe derived amplicons can hybridize to the nucleic acids. Following hybridization to the probe amplicons, the nucleic acids in the sample can be enriched by capturing (e.g., via capturing agents as biotin, antibodies, etc.) and washing and/or eluting the hybridized nucleic acids from the captured probes (FIG. 4). The nucleic acid sequence(s) may be further amplified using, for example, PCR methods to produce an amplified pool of enriched PCR products.

In some cases, the solid support can be a microarray, a slide, a chip, a microwell, a column, a tube, a particle or a bead. In some examples, the solid support can be coated with streptavidin and/or avidin. In some examples, the solid support can be coated with an antibody. Further, the solid support can comprise a glass, metal, ceramic or polymeric material. In some embodiments, the solid support can be a nucleic acid microarray (e.g. a DNA microarray). In other embodiments, the solid support can be a paramagnetic bead.

The enrichment method can comprise digestion with a secondary restriction enzyme, self-ligation (e.g. self-circularization), and re-digestion with the original restriction enzyme. In some examples, the ligation products can be linearized and available for adapter-ligation and sequencing. In other examples, the ligation junction sequence itself can be used for hybridization based enrichment using a bait-probe complimentary to the junction sequence.

As used herein, the term "amplification" refers to any process by which the copy number of a nucleic acid sequence is increased. The disclosure further provides methods for amplifying polynucleotides. In some cases, the polynucleotides can comprise a label. The labeled polynucleotide(s) can be obtained by the methods of the present disclosure.

In some cases, the one or more amplification and/or replication steps are used for the preparation of a library or read-set to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, ligation mediated PCR, Qb replicase amplification, inverse PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In some cases, an amplification reaction may produce only a single complementary copy/replica of a polynucleotide. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles.

In particular cases, PCR can be used to amplify polynucleotides after they are dispensed into individual partitions. In some cases, one or more specific priming sequences within amplification adapters are utilized for PCR amplification. The amplification adapters may be ligated to fragmented polynucleotides before or after dispensing into individual partitions. Polynucleotides comprising amplification adapters with suitable priming sequences on both ends can be PCR amplified exponentially. Polynucleotides with only one suitable priming sequence due to, for example, imperfect ligation efficiency of amplification adapters comprising priming sequences, may only undergo linear amplification. Further, polynucleotides can be eliminated from amplification, for example, PCR amplification, altogether, if no adapters comprising suitable priming sequences are ligated. In some embodiments, the number of PCR cycles vary between 10-30, but can be as low as 9, 8, 7, 6, 5, 4, 3, 2 or less or as high as 40, 45, 50, 55, 60 or more. As a result, exponentially amplifiable fragments carrying amplification adapters with a suitable priming sequence can be present in much higher (1000 fold or more) concentration compared to linearly amplifiable or un-amplifiable fragments, after a PCR amplification. Benefits of PCR, as compared to whole genome amplification techniques (such as amplification with randomized primers or Multiple Displacement Amplification using phi29 polymerase) can include, but are not limited to, a more uniform relative sequence coverage—as each fragment can be copied at most once per cycle and as the amplification is controlled by thermocycling program, a substantially lower rate of forming chimeric molecules than for example MDA (Lasken et al., 2007, BMC Biotechnology 7:19 doi:10.1186/1472-6750-7-19)—as chimeric molecules pose significant challenges for accurate sequence assembly by presenting nonbiological sequences in the assembly graph, which may result in higher rate of misassemblies or highly ambiguous and fragmented assembly, reduced sequence specific biases that may result from binding of randomized primers commonly used in MDA versus using specific priming sites with a specific sequence, a higher reproducibility in the amount of final amplified DNA product, which can be controlled by selection of the number of PCR cycles, and a higher fidelity in replication with the polymerases that are commonly used in PCR as compared to common whole genome amplification techniques known in the art.

In some cases, a fill-in reaction can be followed by or performed as part of amplification of one or more target polynucleotides using a first primer and a second primer, wherein the first primer comprises a sequence that is hybridizable to at least a portion of the complement of one or more of the first adapter oligonucleotides, and further wherein the second primer comprises a sequence that is hybridizable to at least a portion of the complement of one or more of the second adapter oligonucleotides. Each of the first and second primers may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). For example, about 10 to 50 nucleotides can be complementary to the corresponding target sequence.

In some embodiments, an amplification reaction can comprise at least about 5, 10, 15, 20, 25, 30, 35, 40, 50, 60, 70, 80, 90, 100, 150, 200 or more cycles. In some examples, an amplification reaction can comprise at least about 20, 25, 30, 35 or 40 cycles. In some embodiments, an amplification reaction comprises no more than about 5, 10, 15, 20, 25, 35, 40, 50, 60, 70, 80, 90, 100, 150, 200 or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, 1200, 1800, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 40, 50, 60, 70, 80, 90, 100, 150, 200 or more cycles. In some embodiments, amplification is performed following the fill-in reaction.

In some cases, the amplification reaction can be carried out on at least about 1, 2, 3, 4, 5, 6, 7, 8, 9, 10, 12, 14, 16, 18, 20, 25, 30, 40, 50, 100, 200, 300, 400, 500, 600, 800, 1000 ng of the target DNA molecule. In some cases, the amplification reaction can be carried out on less than about 1, 2, 3, 4, 5, 6, 7, 8, 9, 10, 12, 14, 16, 18, 20, 25, 30, 40, 50, 100, 200, 300, 400, 500, 600, 800, 1000 ng of the polynucleotide. Further, amplification can be performed before or after pooling of target polynucleotides from independent samples.

The methods disclosed herein can comprise determining an amount of amplifiable nucleic acid present in a sample. Any known method may be used to quantify amplifiable nucleic acid, and an exemplary method is the polymerase chain reaction (PCR), specifically quantitative polymerase chain reaction (qPCR). qPCR is a technique based on the polymerase chain reaction, and is used to amplify and simultaneously quantify a targeted nucleic acid molecule. qPCR allows for both detection and quantification (as absolute number of copies or relative amount when normalized to DNA input or additional normalizing genes) of a specific sequence in a DNA sample. The procedure follows the general principle of polymerase chain reaction, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), 2006), Heid et al. (Genome Research 986-994, 1996), Sambrook and Russell (Quantitative PCR, Cold Spring Harbor Protocols, 2006), and Higuchi (U.S. Pat. Nos. 6,171,785 and 5,994,056). The contents of these are incorporated by reference herein in their entirety.

Other methods of quantification include use of fluorescent dyes that intercalate with double-stranded DNA, and modified DNA oligonucleotide probes that fluoresce when hybridized with a complementary DNA. These methods can be broadly used but are also specifically adapted to real-time PCR as described in further detail as an example.

In some cases, a DNA-binding dye can bind to double-stranded DNA (dsDNA) in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. To ensure accuracy in the quantification and/or expression of a target gene can be normalized with respect to a stably expressed gene. Copy numbers of unknown genes can similarly be normalized relative to genes of known copy number.

In some cases, a sequence-specific RNA or DNA-based probe can be used to quantify only the DNA containing a probe sequence; therefore, use of the reporter probe significantly increases specificity, and allows quantification even in the presence of some non-specific DNA amplification. This allows for multiplexing, i.e., assaying for several genes in the same reaction by using specific probes with differently colored labels, provided that all genes are amplified with similar efficiency.

These methods can be carried out with a DNA-based probe with a fluorescent reporter (e.g. 6-carboxyfluorescein) at one end and a fluorescence quencher (e.g., 6-carboxy-tetramethylrhodamine) at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g. a sample with a $C_t$ of 3 cycles earlier than another has $2^3=8$ times more template. Amounts of nucleic acid (e.g., RNA or DNA) are then determined by comparing the results to a standard curve produced by a real-time PCR of serial dilutions (e.g. undiluted, 1:4, 1:16, 1:64) of a known amount of nucleic acid.

In certain cases, the qPCR reaction involves a dual fluorophore approach that takes advantage of fluorescence resonance energy transfer (FRET), e.g., LIGHTCYCLER hybridization probes, where two oligonucleotide probes anneal to the amplicon (e.g. see U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes (e.g., Whitcombe et al., Nature Biotechnology 17:804-807, 1999, and U.S. Pat. No. 6,326,145), Sunrise (or AMPLI-FLOUR) primers (e.g., Nazarenko et al., Nuc. Acids Res. 25:2516-2521, 1997, and U.S. Pat. No. 6,117,635), and LUX primers and MOLECULAR BEACONS probes (e.g., Tyagi et al., Nature Biotechnology 14:303-308, 1996 and U.S. Pat. No. 5,989,823).

In other cases, a qPCR reaction uses fluorescent Taqman methodology and an instrument capable of measuring fluorescence in real time (e.g., ABI Prism 7700 Sequence Detector). The Taqman reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra. Any nucleic acid quantification method, including real-time methods or single-point detection methods may be used to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment), as well as any other suitable detection method known in the art for nucleic acid quantification. The quantification may or may not include an amplification step.

The present disclosure provides methods for hybridizing polynucleotides onto an array. A "substrate" or an "array" is an intentionally created collection of nucleic acids which can be prepared either synthetically or biosynthetically in a variety of different formats (e.g., libraries of soluble molecules; and libraries of oligonucleotides tethered to resin beads, silica chips, or other solid supports). Additionally, the term "array" includes those libraries of nucleic acids which can be prepared by spotting nucleic acids of essentially any length (e.g., from 1 to about 1000 nucleotide monomers in length) onto a substrate.

Array technology and the various associated techniques and applications are described generally in numerous textbooks and documents. For example, these include Lemieux et al., 1998, *Molecular Breeding* 4, 277-289; Schena and Davis, *Parallel Analysis with Biological Chips.* in *PCR Methods Manual* (eds. M. Innis, D. Gelfand, J. Sninsky); Schena and Davis, 1999, *Genes, Genomes and Chips.* In *DNA Microarrays: A Practical Approach* (ed. M. Schena), Oxford University Press, Oxford, U K, 1999); *The Chipping Forecast* (Nature Genetics special issue; January 1999 Supplement); Mark Schena (Ed.), *Microarray Biochip Technology*, (Eaton Publishing Company); Cortes, 2000, *The Scientist* 14[17]:25; Gwynn and Page, *Microarray analysis: the next revolution in molecular biology, Science,* 1999 Aug. 6; and Eakins and Chu, 1999, *Trends in Biotechnology,* 17, 217-218.

The library can be fixed or immobilized onto a solid phase (e.g. a solid substrate), to limit diffusion and admixing of the members. In some cases, libraries of DNA binding probes (e.g. oligonucleotides) may be prepared. In particular, the libraries may be immobilized to a substantially planar solid phase, including membranes and non-porous substrates such as plastic and glass. Furthermore, the library can be arranged in such a way that indexing (i.e., reference or access to a particular member) is facilitated. In some examples, the members of the library can be applied as spots in a grid formation. Common assay systems may be adapted for this purpose. For example, an array may be immobilized on the surface of a microplate, either with multiple members in a well, or with a single member in each well. Furthermore, the solid substrate may be a membrane, such as a nitrocellulose or nylon membrane (for example, membranes used in blotting experiments). Alternative substrates include glass, or silica based substrates. Thus, the library can be immobilized by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilized to arrange and fix the libraries on the chip. Oligos may be fixed to an array by their phosphodiester backbones, 5' ends, or 3' ends.

Suitable sequencing methods described herein or otherwise known in the art can be used to obtain sequence information from nucleic acid molecules within a sample. Sequencing can be accomplished through classic Sanger sequencing methods, which are well known in the art. Sequence can also be accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour. In some cases, the sequencing reads can be at least about 50, about 60, about 70, about 80, about 90, about 100, about 120, about 150, about 180, about 210, about 240, about 270, about 300, about 350, about 400, about 450, about 500, about 600, about 700, about 800, about 900, about 1000, about 1500, about 2000, about 2500, about 3000, about 4000, about 5000, about 6000, about 7000, about 8000, about 9000, or about 10000 bases per read.

In some cases, high-throughput sequencing can be performed using technology available by Illumina's Genome Analyzer IIX, MiSeq personal sequencer, or HiSeq systems, such as those using HiSeq 2500, HiSeq 1500, HiSeq 2000, or HiSeq 1000 machines. These machines use reversible terminator-based sequencing by synthesis chemistry. These machines can produce 200 billion DNA reads or more in eight days. Smaller systems may be utilized for runs within 3, 2, 1 days or less time.

In some cases, high-throughput sequencing can be performed using technology available by ABI Solid System. This genetic analysis platform that enables massively parallel sequencing of clonally-amplified DNA fragments linked to beads. The sequencing methodology is based on sequential ligation with dye-labeled oligonucleotides.

In some cases, high-throughput sequencing can be performed using ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an IONPROTON™ Sequencer is used to sequence nucleic acid. In some cases, an IONPGM™ Sequencer is used. The Ion Torrent Personal Genome Machine (PGM). The PGM can do 10 million reads in two hours. In some cases, high-throughput sequencing can be performed using technology available by Helicos BioSciences Corporation (Cambridge, Mass.) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some cases, high-throughput sequencing can be performed using technology available by 454 Lifesciences, Inc. (Branford, Conn.) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors", Nature 437, 376-380 (15 Sep. 2005), doi:10.1038/nature03959; and well as in US Application Publication Nos. 20020012930; 20030068629; 20030100102; 20030148344; 20040248161; 20050079510, 20050124022; and 20060078909.

In some cases, high-throughput sequencing can be performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

In some cases, high-throughput sequencing can be performed using real-time (SMRT™) technology by Pacific Biosciences. In SMRT, each of four DNA bases can be attached to one of four different fluorescent dyes. These dyes can be phospho linked. A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent tag can be cleaved off. The ZMW can be illuminated from below. Attenuated light from an excitation beam can penetrate the lower 20-30 nm of each ZMW. A microscope with a detection limit of 20 zepto liters ($10"$ liters) can be created. The tiny detection volume can provide 1000-fold improvement in the reduction of background noise. Detection of the corresponding fluorescence of the dye can indicate which base was incorporated. The process can be repeated.

In some cases, high-throughput sequencing can be performed using nanopore sequencing (See, e.g., Soni G V and Meller A. (2007) Clin Chem 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridlON system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., $SiN_x$, or $SiO_2$). The nanopore can be a hybrid pore (e.g., an integration of a protein pore into a solid-state membrane). The nanopore can be a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be also used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

In some cases, high-throughput sequencing can be performed using DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Adl) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., Acul), and the DNA can be cleaved by Acul 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Adl adapter. A restriction enzyme (e.g., Acul) can be applied, and the DNA can be cleaved 13 bp to the left of the Adl to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamethyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

In some cases, high-throughput sequencing can be performed using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In particular embodiments, the present disclosure further provides kits comprising one or more components of the disclosure. The kits can be used for any application apparent to those of skill in the art, including those described above. The kits can comprise, for example, a plurality of association molecules, a fixative agent, a restriction endonuclease, a ligase, and/or a combination thereof. In some cases, the association molecules can be proteins including, for example, histones or other nucleic acid binding proteins as disclosed herein, such as histones, for example comprising at least one of H2A, H2B, H3A, H3B, H4A and H4B, a transcription factor, a double-stranded DNA binding protein such as a topoisomerase (bacterial, type I or type II), a restriction endonuclease, a transposase, a transcription factor or packing proteins such as H1 and protamine. In some kit embodiments the association molecule or molecules are chemically modified or genetically engineered such that it retains nucleic acid binding activity.

In some cases, the fixative agent can be formaldehyde or any other DNA crosslinking agent.

In some cases, the kit can comprise sequencing adaptors and/or sequencing primers. Further, the kit can comprise a device capable of amplifying the read-sets using the sequencing adaptors and/or sequencing primers.

In some cases, the kit can also comprise other reagents including but not limited to lysis buffers, ligation reagents (e.g. dNTPs, polymerase, polynucleotide kinase, and/or ligase buffer, etc.), and PCR reagents (e.g. dNTPs, polymerase, and/or PCR buffer, etc.).

The kit can also include instructions for using the components of the kit and/or for generating the read-sets.

Figure 7:
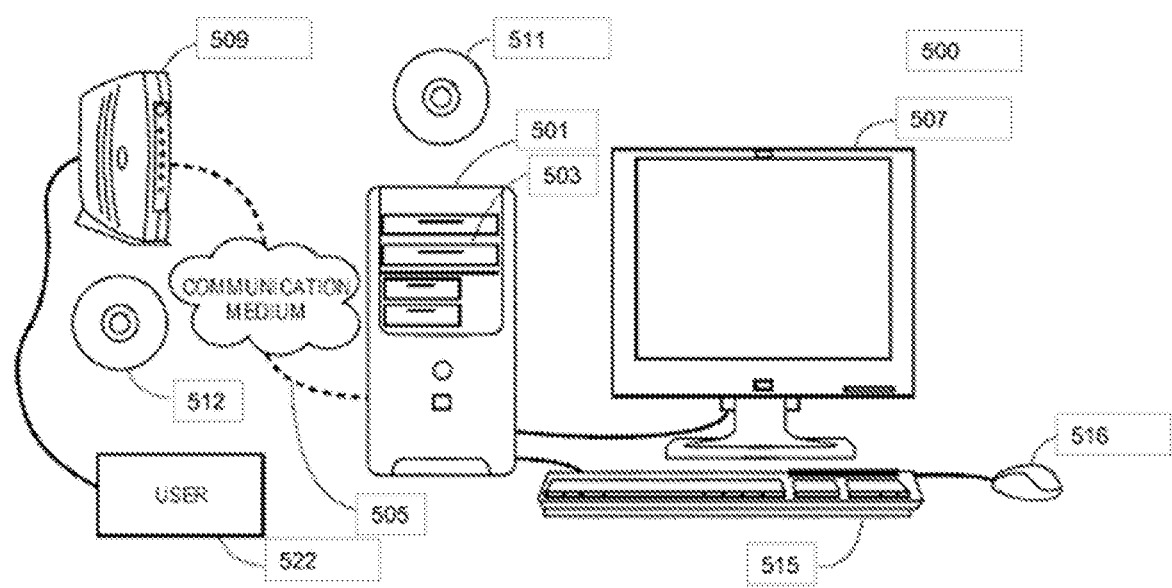
FIG. 7 illustrates various components of an exemplary computer system according to various embodiments of the present disclosure.

The computer system 500 illustrated in FIG. 7 may be understood as a logical apparatus that can read instructions from media 511 and/or a network port 505, which can optionally be connected to server 509 having fixed media 512. The system, such as shown in FIG. 7 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 7.

Figure 8:
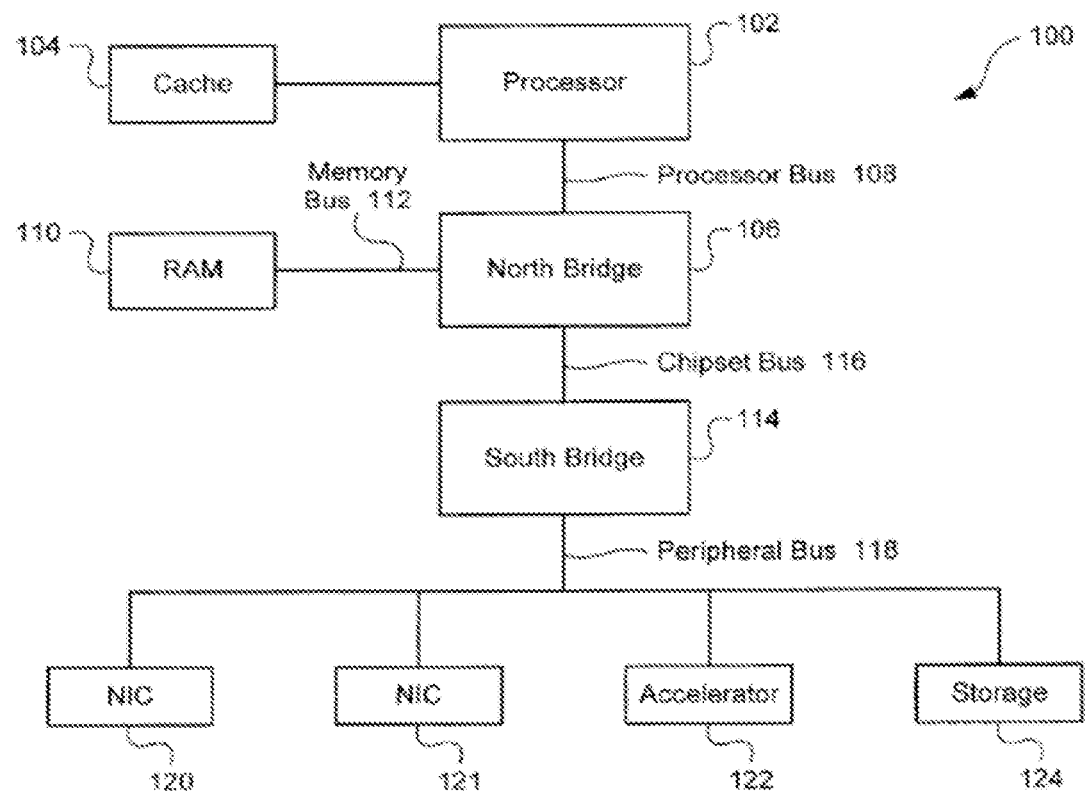
FIG. 8 is a block diagram illustrating the architecture of an exemplary computer system that can be used in connection with various embodiments of the present disclosure.

FIG. 8 is a block diagram illustrating a first example architecture of a computer system 100 that can be used in connection with example embodiments of the present disclosure. As depicted in FIG. 8, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 8, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 9:
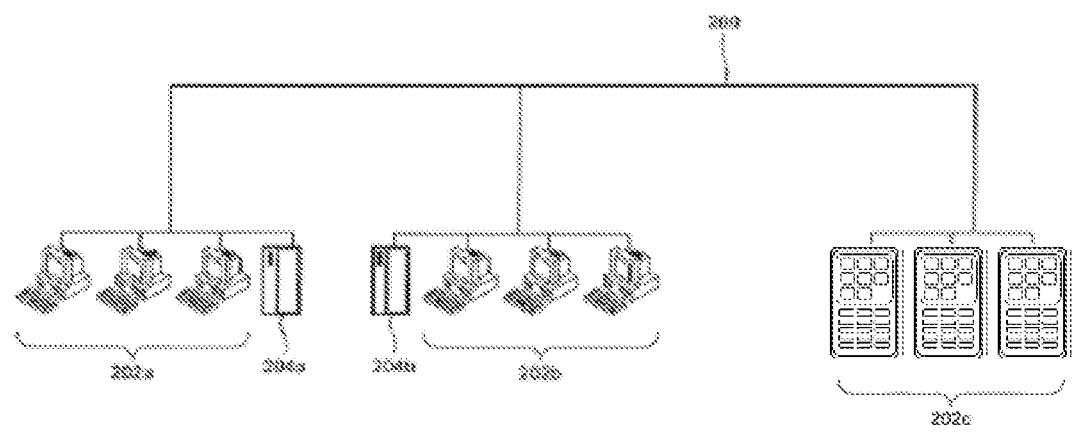
FIG. 9 is a diagram illustrating an exemplary computer network that can be used in connection with various embodiments of the present disclosure.

FIG. 9 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 9 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface.

In some examples, processors can maintain separate memory spaces and transmit data through network interfaces, back plane or other connectors for parallel processing by other processors. In other embodiments, some or all of the processors can use a shared virtual address memory space.

Figure 10:
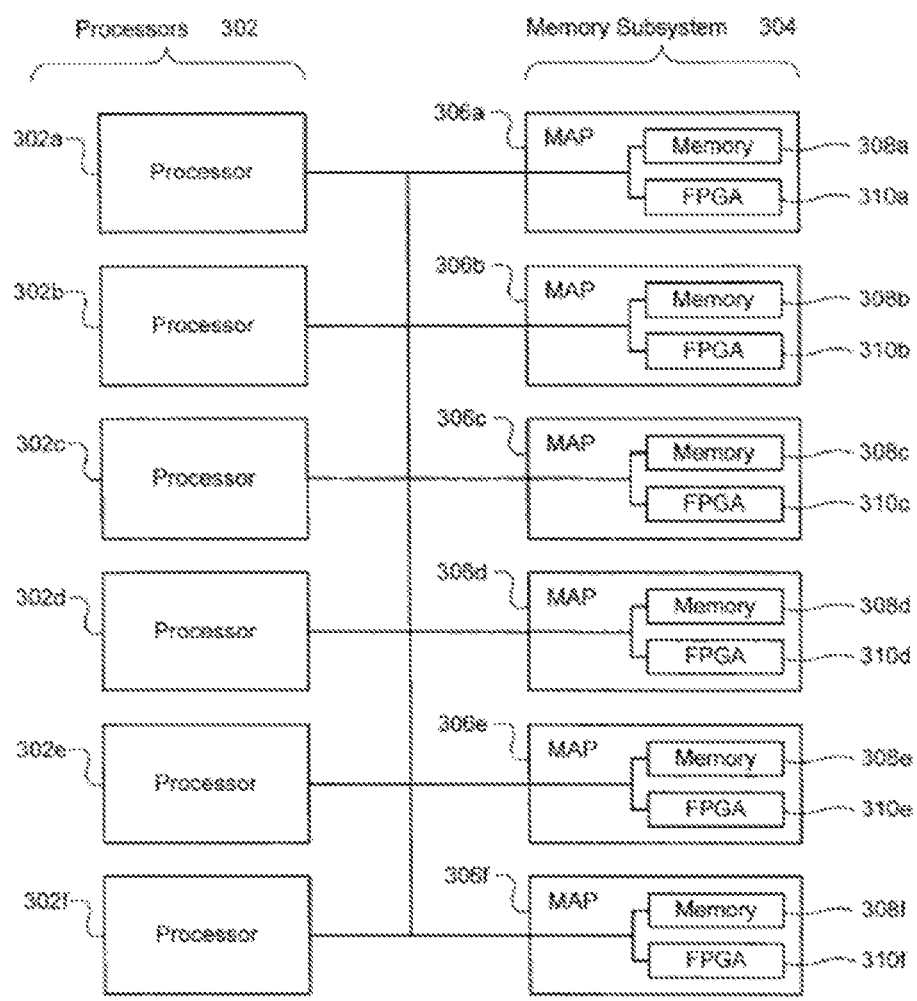
FIG. 10 is a block diagram illustrating the architecture of another exemplary computer system that can be used in connection with various embodiments of the present disclosure.

FIG. 10 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In some cases, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 10, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 8.

Some embodiments disclosed herein relate to a multistep integrated system for providing phase information related to a sample from an individual or other source. Systems comprise at least one of the steps recited herein. An individual is identified for phase information to be determined.

EXAMPLES

Example 1

Oligonucleotide Platform

A platform of 90,000 oligonucleotide spots, comprising 250 million oligonucleotides per spot is generated. Oligonucleotides are 50 nucleotides in length and are attached to the platform at their 3' ends. Oligonucleotides comprise, from 3' to 5', a 5 nucleotide spacer, a 25 nucleotide portion of P5 sequence, a 16 nucleotide barcode region, and a 5' terminal 4 nucleotide MboI cleavage site (3' CTAG 5'). Oligo populations differ between one another in their 16 nucleotide barcode region sequences but share the other features in common.

Chambers for reactions are created by placing a LifterSlip over the area of the microarray that contains the spots. Reaction mixtures are applied by pipetting from one side of the LifterSlip. Washes in between reactions are carried out by dunging the slide in a 500 mL beaker of 10 mM Tris-HCl, pH 8.0.

Example 2

Sample Internal Free End Generation

Genomic DNA formed into globs is digested with MboI restriction enzyme. 5' phosphates are removed by treatment with phosphatase. Genomic DNA is purified and chromatin dialized.

Example 3

Workflow

An oligonucleotide platform as in Example 1 is provided. Oligo 5' ends are phosphorylated. Nucleic acid-polypeptide globs are diluted to a concentration of about 1-5 globs per microarray spot and allowed to anneal to probes on the platform. Arrays are treated with 50 mM Tris, pH 7.0, 10 mM EDTA, 1% SDS to provide alkaline conditions necessary for crosslink reversal.

Using the P5 binding site present on the oligos on the spots, a second strand is synthesized. A P5 primer is provided under conditions allowing annealing to a platform oligo P5 binding site. Bst polymerase large fragment having strand displacing helicase activity, and a composition comprising reagents and buffers necessary for nucleic acid extension is applied to the platform. Biotinylated dCTP is included among the reagents.

Example 4

Template Recovery 1

The glob-bound platforms are treated with 50 mM Tris, pH 8.0, 10 mM EDTA, 1% SDS with heat to cleave the bond between the 3' end of the oligos and the platform. The globs are purified and sheared with a bioruptor to shear tagged ends from the glob. The template is blunt ended by treatment with a single-strand exonuclease or a DNA polymerase. The template is treated to add a 3' adenyl overhang and ligated to a P7 adapter by TA ligation.

Example 5

Template Recovery 2

Blunt-ended template molecules are treated to add a 3' adenyl overhang and ligated to a P7 adapter by TA ligation. The template molecules are treated with sodium hydroxide to denature the molecules. The denatured molecules are contacted with magnetically tagged streptavidin beads, molecules comprising biotinylated deoxy Cytosine are bound, and the complexes are recovered through magnetic pull-down.

Example 6

Sequencing Library Preparation

Oligonucleotides that bind to the P5 and P7 binding sites are annealed to the templates, and reagents for PCR are introduced. The composition is subjected to a thermocycling reaction to exponentially amplify templates having full P5 and P7 oligo sequence.

Example 7

Spatial Bias During Ligation

A ligation mixture is added to one end of a LifterSlip area and a double-stranded DNA probe labeled with a fluorescent dye is added. A gradient of decreasing amounts of ligated probe is observed, having a highest concentration at the vicinity of the ligation mixture introduction, decreasing with distance from that site.

The ligation mixture is added as above, to a platform incubated at a temperature above the melting temperature of the ligation product. The ligation mixture is allowed to evenly distribute throughout the surface of the platform prior to cooling the platform to the Tm necessary for annealing and ligation. A double-stranded DNA probe labeled with a fluorescent dye is added. A uniform amount of ligated probe is observed throughout the area of application.

A number of embodiments have been described herein. Nevertheless, it will be understood that various modifications may be made without departing from the spirit and scope of this disclosure. Accordingly, other embodiments are within the scope of the following claims.

What is claimed is:

1. A method of tagging internal regions of an original nucleic acid molecule, comprising
cross-linking the original nucleic acid molecule to at least one polypeptide, wherein the original nucleic acid molecule and the at least one polypeptide form a complex that binds a first segment of the original nucleic acid molecule to a second segment of the original nucleic acid molecule independent of a phosphodiester linkage between the first segment and the second segment;
cleaving the original nucleic acid molecule to generate at least one double-strand break comprising a first internal free end and a second internal free end;
attaching an oligonucleotide barcode tag to the first internal free end to form at least one oligo-attached first internal free end, wherein the oligonucleotide barcode tag is attached to a surface;

annealing an oligonucleotide comprising a sequencing primer and a sequence complementary to the oligonucleotide barcode tag to form an annealed oligonucleotide;

polymerizing the annealed oligonucleotide to form an extended polynucleotide comprising sequences for the sequencing primer, the oligonucleotide barcode tag, and at least a portion of the original nucleic acid molecule adjacent to the first internal free end;

separating the extended polynucleotide from the at least one polypeptide; and sequencing the extended polynucleotide to obtain a sequence of the nucleic acid molecule at a region immediately adjacent to the at least one oligo-attached first internal free end.

2. The method of claim 1, wherein the at least one polypeptide is a nucleic acid binding protein.

3. The method of claim 1, wherein the at least one polypeptide is a nuclear protein.

4. The method of claim 1, wherein the at least one polypeptide is a chromatin constituent.

5. The method of claim 1, wherein cleaving the original nucleic acid molecule to generate at least one double-strand break comprising a first internal free end and a second internal free end comprises contacting the original nucleic acid molecule with a restriction endonuclease.

6. The method of claim 1, wherein said attaching comprises ligating.

7. The method of claim 1, wherein said attaching comprises hybridization and extension with a DNA polymerase.

8. The method of claim 1, wherein said surface comprises an interior of a well.

9. The method of claim 1, wherein said surface comprises a bead.

10. The method of claim 1, wherein the oligonucleotide barcode tag comprises a sequence that identifies the region immediately adjacent to the at least one oligo-attached first internal free end as corresponding to the original nucleic acid molecule.

11. The method of claim 5, wherein the restriction endonuclease is a 6-base cutter.

12. The method of claim 5, wherein the restriction endonuclease is a 4-base cutter.

13. The method of claim 1, wherein cleaving the original nucleic acid molecule to generate at least one double-strand break comprising a first internal free end and a second internal free end comprises contacting the original nucleic acid molecule with a reagent having endonuclease activity.

14. The method of claim 13, wherein the reagent is an enzyme.

15. The method of claim 13, wherein the endonuclease activity is nonspecific endonuclease activity.

16. The method of claim 13, wherein the endonuclease activity is specific endonuclease activity.

17. The method of claim 1, further comprising isolating the original nucleic acid molecule cross-linked to the at least one polypeptide in a reaction volume.

* * * * *